(12) United States Patent
Kouchi et al.

(10) Patent No.: US 8,793,144 B2
(45) Date of Patent: Jul. 29, 2014

(54) TREATMENT EFFECT PREDICTION SYSTEM, A TREATMENT EFFECT PREDICTION METHOD, AND A COMPUTER PROGRAM PRODUCT THEREOF

(75) Inventors: Yasuhiro Kouchi, Kakogawa (JP); Takeo Saitou, Kobe (JP); Masayoshi Seike, Kobe (JP)

(73) Assignee: Sysmex Corporation, Kobe-shi, Hyogo (JP)

( * ) Notice: Subject to any disclaimer, the term of this patent is extended or adjusted under 35 U.S.C. 154(b) by 2332 days.

(21) Appl. No.: 11/431,594

(22) Filed: May 11, 2006

(65) Prior Publication Data

US 2006/0265136 A1 Nov. 23, 2006

(30) Foreign Application Priority Data

May 12, 2005 (JP) ................................. 2005-139424

(51) Int. Cl.
- *G06Q 50/00* (2012.01)
- *G06F 19/20* (2011.01)
- *G06F 19/00* (2011.01)
- *G06Q 50/24* (2012.01)

(52) U.S. Cl.
CPC ............... *G06F 19/20* (2013.01); *G06F 19/34* (2013.01); *G06Q 50/24* (2013.01)
USPC .................................................. 705/3; 705/2

(58) Field of Classification Search
CPC ....... G06F 19/20; G06F 19/24; G06F 19/322; G06F 19/3437
See application file for complete search history.

(56) References Cited

U.S. PATENT DOCUMENTS

| | | | |
|---|---|---|---|
| 5,940,802 A * | 8/1999 | Hildebrand et al. | 705/3 |
| 5,971,922 A * | 10/1999 | Arita et al. | 600/365 |
| 6,421,633 B1 * | 7/2002 | Heinonen et al. | 703/11 |
| 7,914,449 B2 * | 3/2011 | Kouchi et al. | 600/365 |
| 2003/0058245 A1 * | 3/2003 | Brazhnik et al. | 345/440 |
| 2004/0091424 A1 * | 5/2004 | Asano et al. | 424/9.1 |
| 2005/0234311 A1 * | 10/2005 | Kouchi et al. | 600/300 |
| 2013/0332083 A1 * | 12/2013 | Van Laar | 702/19 |

FOREIGN PATENT DOCUMENTS

| | | |
|---|---|---|
| WO | 03/023682 A2 | 3/2003 |
| WO | 03/104939 A2 | 12/2003 |
| WO | 2004/031913 A2 | 4/2004 |
| WO | 2005/036446 A2 | 4/2005 |

OTHER PUBLICATIONS

Correspond Definition—Collins EnglishDictionary, HarperCollins Publishers 2000.*

(Continued)

*Primary Examiner* — Neal Sereboff
(74) *Attorney, Agent, or Firm* — Sughrue Mion, PLLC

(57) ABSTRACT

A treatment effect prediction system, comprising: a processor; and a memory, under control of the processor, including instructions enabling the processor to carry out operations comprising: determining a patient pathological condition information, which represents a feature of pathological condition of a patient, based on diagnostic data of the patient; accessing a database of stored pathological condition information and corresponding treatment effects occurring when predetermined treatment is provided; and retrieving, from the database, a specific treatment effect corresponding to the one of the stored pathological condition information that is similar to the patient pathological condition information, is disclosed. A treatment effect prediction method and a computer program product thereof are also disclosed.

16 Claims, 23 Drawing Sheets

(56) References Cited

OTHER PUBLICATIONS

Correlate Definition—Chambers 21$^{st}$ Century Dictionary, Chambers Harrap Publishers Limited 2001.*

Owens, Camelia "Control of blood glucose concentrations for people with type 1 diabetes mellitus" Summer 2004 UMI dissertation.*

Richard N. Bergman, et al, "Quantitative Estimation of Insulin Sensitivity", American Journal of Physiology, vol. 236, No. 6, 1979, pp. E667-E677.

Richard N. Bergman, et al, "Physiologic Evaluation of Factors Controlling Glucose Tolerance in Man", Journal of Clinical Investigation, vol. 68, No. 6, Dec. 1981, pp. 1456-1467.

* cited by examiner (a)

(b)

TREATMENT EFFECT PREDICTION SYSTEM, A TREATMENT EFFECT PREDICTION METHOD, AND A COMPUTER PROGRAM PRODUCT THEREOF

FIELD OF THE INVENTION

The present invention relates to a treatment effect prediction system for predicting a treatment effect of treating a patient, a treatment effect prediction method for predicting a treatment effect of treating a patient, and a computer program product thereof.

BACKGROUND

When treating an illness, physicians generally perform various examination in addition to than interview. Then, the physician selects a treatment method based on the diagnostic data included in the clinical findings and the obtained examination result and relying on his own experience and perception.

The data used to analyze pathological conditions arising from causes that may manifest various symptoms of illness that are described in a patient's subjective complaints are normally only those examination values that can be measured directly, however, it may be difficult to precisely grasp and predict the patient's pathological condition and course just using the examination values depending on the disease. In the case of diabetes, for example, blood sugar level is an indicator of the severity of illness, however, the blood sugar level is nothing more than an examination result, and pathological conditions such as insulin secretory defect, peripheral insulin resistance, impaired hepatic glucose uptake, and excessive hepatic glucose release are still difficult to grasp from clinical findings even for specialists systems have been developed that support examination and treatment by providing the physician with information (treatment supporting information) useful in providing treatment (for example, U.S. Pat. Nos. 6,421,633 and 5,971,922). Conventional systems only have functions for monitoring examination results, and simply providing drug dosages according to the examination results, and are fully utilized by physicians, but they can not provide treatment support information that can be used to determine the pathological condition and course of individual patients.

In the medical field, information concerning treatment effects (what level of treatment, at what stage to perform treatment and the like) is of the utmost importance, and a great deal of data has been acquired relating to treatment effects when specific treatment methods are used. In the case of cancer, for example, much data has been collected concerning the relationship between treatment method (surgery, radiation therapy, chemotherapy and the like) and treatment effect (5-year survival rate and the like) in accordance with the progression and type of cancer. Furthermore, in the pharmaceutical field, data has been collected concerning the relationship between the treatment period and drug efficacy regarding subjects of different sex and age. It is possible to predict a particular level of treatment effect based on these data.

These data are based on the type of disease and examination values that are directly measurable, and although these are used as yardsticks to some degree in treatment effect, there is a loss of accuracy, and predicting treatment effect is often still dependent on the experience of the physician.

SUMMARY

The scope of the present invention is defined solely by the appended claims, and is not affected to any degree by the statements within this summary.

A first aspect of the present invention is a treatment effect prediction system, comprising: pathological condition information obtaining means for obtaining patient pathological condition information which is generated from diagnostic data of a patient and represents a feature of pathological condition of the patient; finding means for finding stored pathological condition information which is similar to the patient pathological condition information obtained by the pathological condition information obtaining means, from a database which stores the stored pathological condition information and a corresponding treatment effect occurring when predetermined treatment is provided; and treatment effect obtaining means for obtaining the treatment effect which corresponds to the stored pathological condition information found by the finding means from the database.

A second aspect of the present invention is a treatment effect prediction system, comprising: a processor; and a memory, under control of the processor, including instructions enabling the processor to carry out operations comprising: determining a patient pathological condition information, which represents a feature of pathological condition of a patient, based on diagnostic data of the patient; accessing a database of stored pathological condition information and corresponding treatment effects occurring when predetermined treatment is provided; and retrieving, from the database, a specific treatment effect corresponding to the one of the stored pathological condition information that is similar to the patient pathological condition information.

A third aspect of the present invention is a treatment effect prediction method, comprising: determining a patient pathological condition information, which represents a feature of pathological condition of a patient, based on diagnostic data of the patient; accessing a database of stored pathological condition information and corresponding treatment effects occurring when predetermined treatment is provided; and retrieving, from the database, a specific treatment effect corresponding to the one of the stored pathological condition information that is similar to the patient pathological condition information.

A fourth aspect of the present invention is a computer program product for the prediction of treatment effects, comprising: a computer readable medium; and computer instructions, on the computer readable medium, for enabling a computer to perform the operation of: determining a patient pathological condition information, which represents a feature of pathological condition of a patient, based on diagnostic data of the patient; accessing a database of stored pathological condition information and corresponding treatment effects occurring when predetermined treatment is provided; and retrieving, from the database, a specific treatment effect corresponding to the one of the stored pathological condition information that is similar to the patient pathological condition information.

DETAILED DESCRIPTION OF THE PREFERRED EMBODIMENTS

Figure 1:
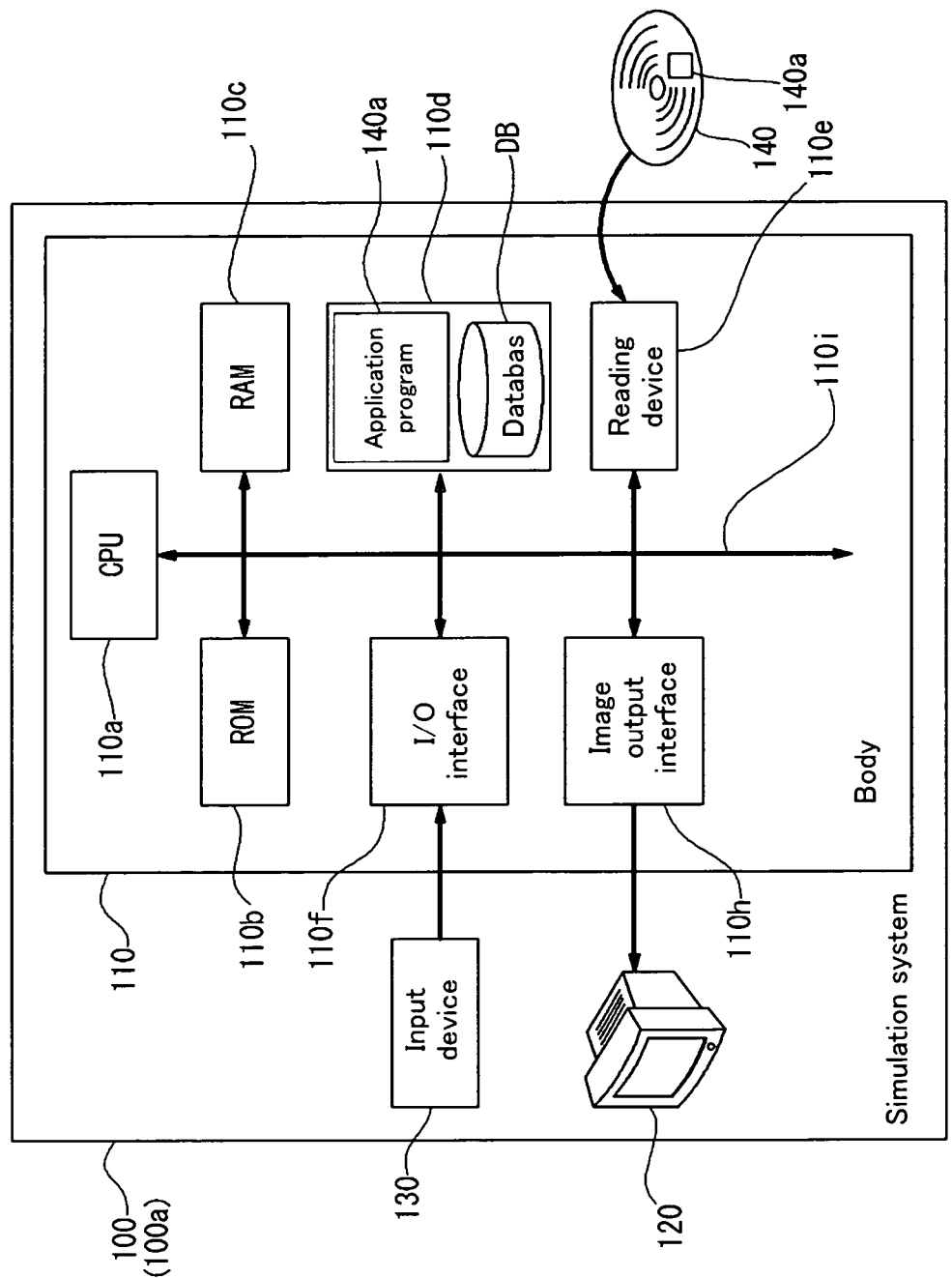
FIG. 1 is a block diagram showing the hardware structure of an embodiment of the system of the present invention.

The preferred embodiments of the present invention are described hereinafter with reference to the drawings.

A system 100 of the present embodiment predicts the treatment effect that can be expected for a patient treated by a therapy by means of a computer, and is configured by a computer 10*a* that mainly includes a body 110, display 120, and input device 130. The body 110 is mainly configured by a central processing unit (CPU) 110*a*, ROM 110*b*, RAM 110*c*, hard disk 110*d*, reading device 110*e*, I/O interface 110*f*, and image output interface 110*h*; and the CPU 110*a*, ROM 110*b*, RAM 110*c*, hard disk 110*d*, reading device 110*e*, I/O interface 110*f*, and image output interface 110*h* are connected a bus 110*i* so as be capable of data communication.

The CPU 110*a* is capable of executing computer programs stored in the ROM 110*b* and computer programs loaded in the RAM 110*c*. Each function block described later is realized when the CPU 110*a* executes an application program 140*a* also described later, such that the computer 100*a* functions as the simulation system 100.

The ROM 110*b* may be configured by a mask ROM, PROM, EPROM, EEPROM and the like, and stores the computer programs executed by the CPU 110*a* and the data used by these programs.

The RAM 110*c* may be configured by an SRAM, DRAM and the like. The RAM 110*c* is used to read the computer programs stored in the ROM 110*b* and on the hard disk 110*d*. The RAM 110*c* is also used a work area for the CPU 110*a* when the computer programs are executed.

The hard disk 110*d* contains an installed operating system and application programs and the like, and various types of computer programs executed by the CPU 110*a* as well as data used in the execution of those computer programs. The application program 140*a*, which is described later, is also installed on the hard disk 110*d*. The hard disk 110*d* also stores databases DB, which are described later, and these databases DB are accessible by the CPU 110*a*.

The reading device 110*e* is configured by a floppy disk drive, CD-ROM drive, DVD-ROM drive and the like, and reads computer programs and data recorded on a portable recording medium 140. The portable recording medium 140 stores an application program 140*a* that enables a computer to function as the simulation system of the present embodiment, and the computer 100*a* can read the application program 140*a* from the portable recording medium 140, and the application program 140*a* can be installed on the hard disk 110*d*.

The application program 140*a* need not be provided on the portable recording medium 140, an as much as it may also be provided from an external device connected to the computer 100*a* so as to be capable of communication via an electric communication line (either wire lineor wireless). For example, the application program 140*a* may be stored ahead of time on the hard disk of a server computer connected to the Internet, such that the computer 100*a* can access the server computer, download the computer program, and install the computer program on the hard disk 110*d*.

Furthermore, an operating system for providing a graphical user interface environment, such as, for example, Microsoft Windows (registered trademark) or the like, is installed on the hard disk 110*d*. In the following description, the application program 140*a* of the present embodiment operates in the environment of this operating system.

The I/O interface 110*f* is configured by, for example, a serial interface such as a USB, IEEE1394, RS-232C or the like, parallel interface such as a SCSI, IDE, IEEE1284 or the like, and analog interface such as a D/A converter, A/D converter or the like. The input device 130 including a keyboard and mouse is connected to the I/O interface 10*f*, such that data can be input to the computer 100*a* by a user using the input device 130.

The image output interface 110*h* is connected to the display 120 configured by an LCD, CRT or the like, such that image signals corresponding to the image data provided by the CPU 110*a* are out put to the display 120. The display 120 displays the image (screen) in accordance with the input image signals.

Figure 2:
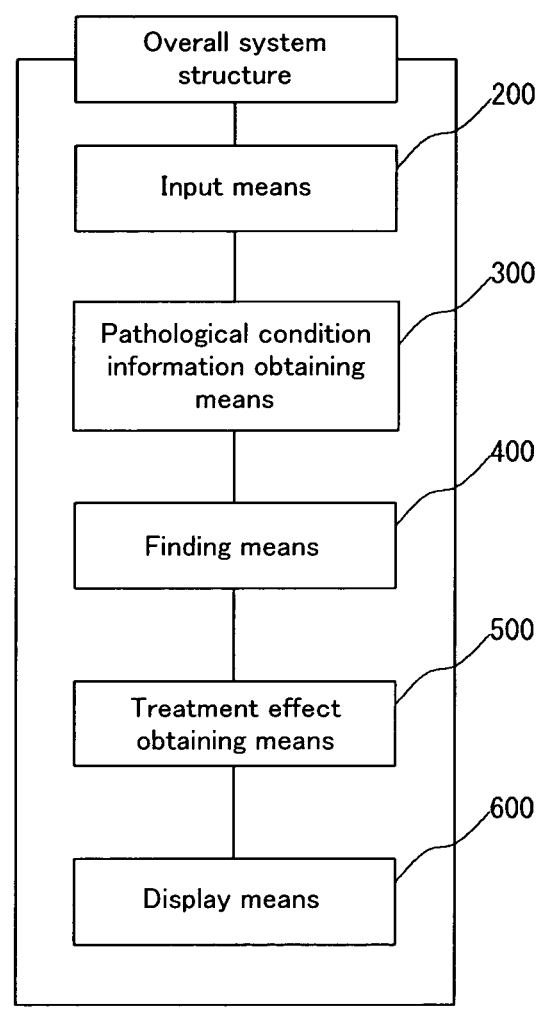
FIG. 2 shows the overall structure of an embodiment of the system of the present invention.

The computer 100*a* functions as a system 100 provided with the various function blocks shown in FIG. 2, when the CPU 110*a* executes the application program 140*a*. As shown in FIG. 2, the system 100 includes the function blocks of an input means 200 for receiving patient diagnostic data input, pathological condition information obtaining means 300 for obtaining pathological condition information indicating the characteristics of the pathological condition of a patient, finding means 400 for finding pathological condition information similar to the pathological condition information obtained by the pathological condition information obtaining means 300 from databases storing mutually associated treatment effects when a particular treatment method is used for the patient, treatment effect obtaining means 500 for obtaining treatment effects associated with a pathological condition from a database, and a display means 600 for displaying the obtained treatment effects.

Figure 3:
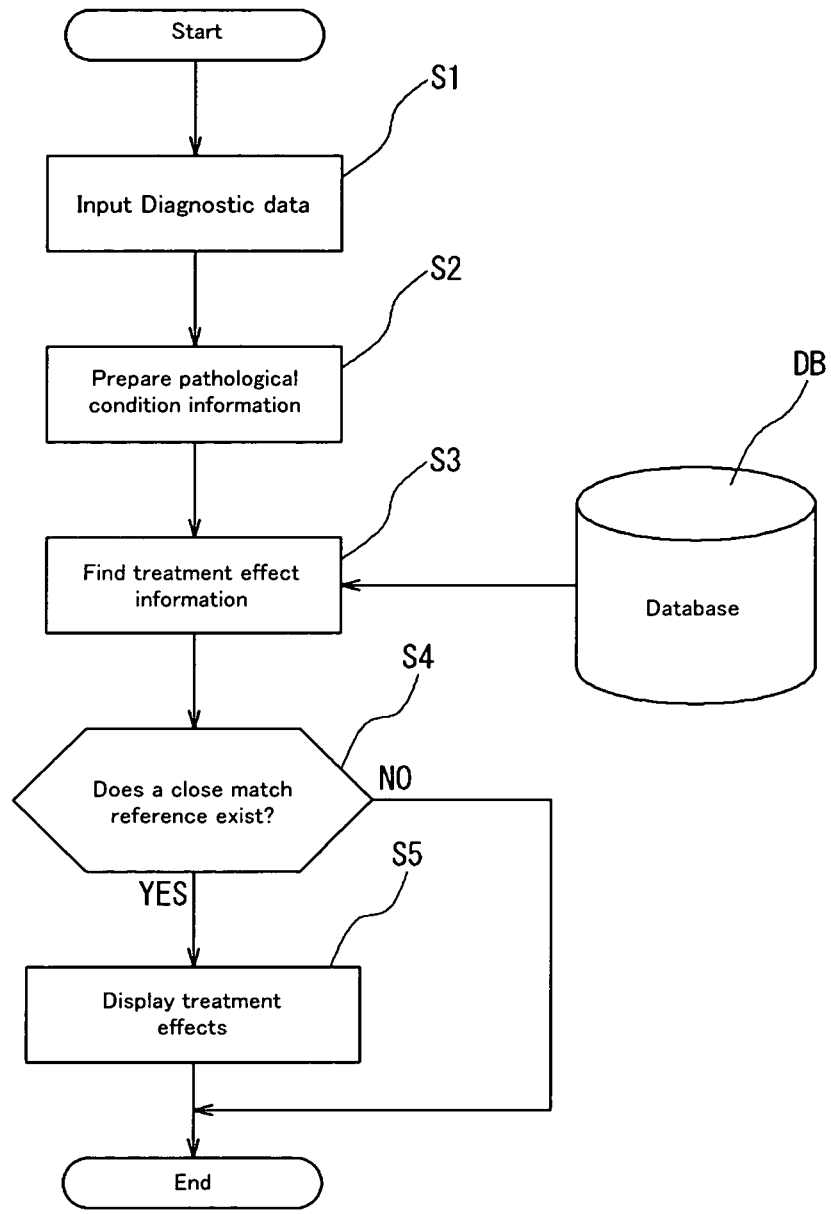
FIG. 3 is a flow chart showing an example of treatment effect prediction by the system of the present invention.

According to this system, patient treatment effects can be predicted as follows. As shown in FIG. 3, patient diagnostic data are input via the input means 200, and the input data are received by the CPU 110*a* (step S1). The diagnostic data are obtained from various types of examinations normally performed using the blood and urine of the patient in order to learn the internal conditions and levels of the patient; in the case of diabetes, for example, such data include the blood sugar level, blood insulin concentration and the like.

The CPU 100*a* prepares pathological condition information endemic to a patient using the diagnostic data. This pathological condition information is information related to the pathological condition, including causes of various symptoms of illness appearing as subjective symptoms, whereas conditions associated with the results of diagnostic data and the results themselves are different information. In the case of diabetes, for example, blood sugar level is an indicator of the severity of the disease, however, the blood sugar level is nothing more than an examination result, and information related to pathological conditions such as insulin secretory defect, peripheral insulin resistance, impaired hepatic glucose uptake, and excessive hepatic glucose release are of extreme importance to treatment. "Pathological condition information" can be narrowly defined as "quantitatively understood pathological condition," and can be broadly defined as "quantitatively understood pathological condition and patient information including diagnostic values." In the case of diabetes, for example, there is pathological condition information such as insulin secretory defect, peripheral insulin resistance, impaired peripheral glucose uptake, impaired hepatic glucose uptake, and excessive hepatic glucose release, and these types of information together with the age, sex, weight, HbA1c, waist diameter, and blood pressure of the patient and the like are included in the broad definition of pathological condition. In the present Specification, the narrow definition of pathological condition is used unless otherwise specified.

Figure 4:
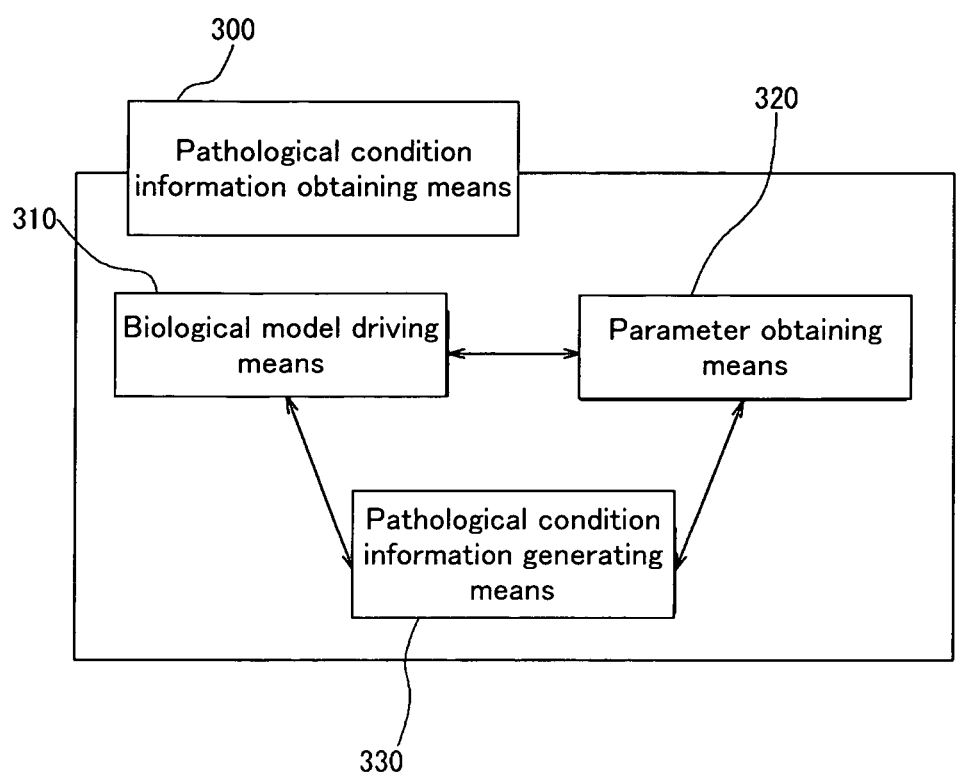
FIG. 4 is a block diagram showing an example of the information acquiring means in the system of the present invention.

Specifically, pathological condition information can be obtained by the pathological condition information obtaining means 300, which is configured by a biological model driving means 310 for simulating the behavior of a living body using a biological model realized by a mathematical model having a plurality of parameters of organ functions, parameter obtaining means 320 for obtaining parameters of a biological model appropriate the patient based on diagnostic data input via the input means 200, and pathological condition information generating means 330 for generating pathological condition information of a patient based on parameters obtained by the parameter obtaining means 320, as shown in FIG. 4.

The CPU 110*a* accesses the database DB that stores mutually associated treatment effects when using specific treatment methods for the patient and pathological condition information specific to that patient, and finds the pathological condition information similar to the pathological condition information obtained in step S2 (by the pathological condition information obtaining means 300) (step S3). Although described in detail later, a plurality of patient pathological condition information, and treatment results when specific treatment methods were used for those patient conditions are mutually associated and stored ahead of time in the database DB. Treatment methods include the means used in the treatment of illness, including, for example, surgery, exercise, dietary treatment and the like in addition to the typical drug treatment methods. These treatment methods may be used individually or in various combinations. Treatment methods for diabetes, for example, can include dietary treatment, exercise program, sulfonyl urea, fast-acting insulin secretory accelerator, insulin resistance enhancer, glucose absorption inhibitor, manufactures insulin and multiple combinations thereof. Since different treatment methods can be used for the same pathological condition, a number of templates that multiply the number of treatment methods used for each pathological condition information in a plurality of pathological condition information that can be stored in the database DB.

Figure 18:
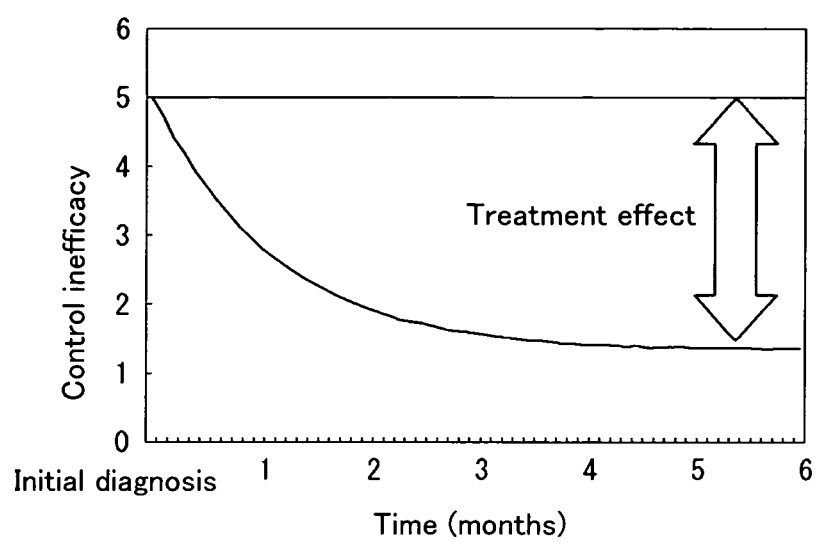
FIG. 18 shows data collected for one random patient.

FIG. 18 shows data collected for one random patient. The data hypothesize diabetes, and the vertical axis is the extent of control inefficacy; consider insulin secretory defect, peripheral insulin resistance, impaired hepatic glucose uptake, and excessive hepatic glucose release. The extent of control inefficacy is numerized to a suitable numeric value according to the degree of insulin secretory defect, such that smaller number represents greater treatment effect than bigger number.

Figure 19:
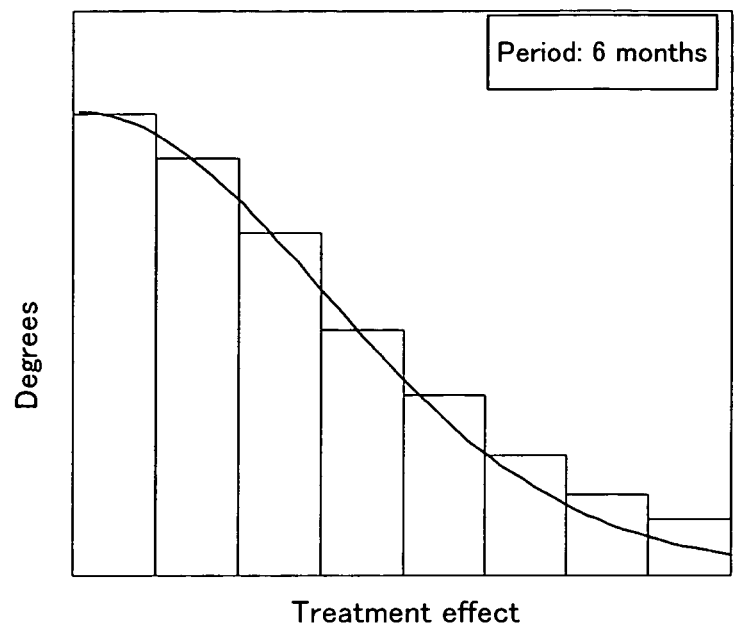
FIG. 19 shows an example of a template created based on data collected for many patients.

FIG. 19 shows an example of a template created based on data collected for many patients. This example, shows the degree of treatment effect obtained when a patient with a similar pathological condition was treated in the past. The degree indicates the number of collected past examples in which a specific treatment effect (the treatment effect may be numerized like the extent of control inefficacy, the blood sugar level diagnostic values may be allocated within a predetermined range) is obtained.

Figure 20:
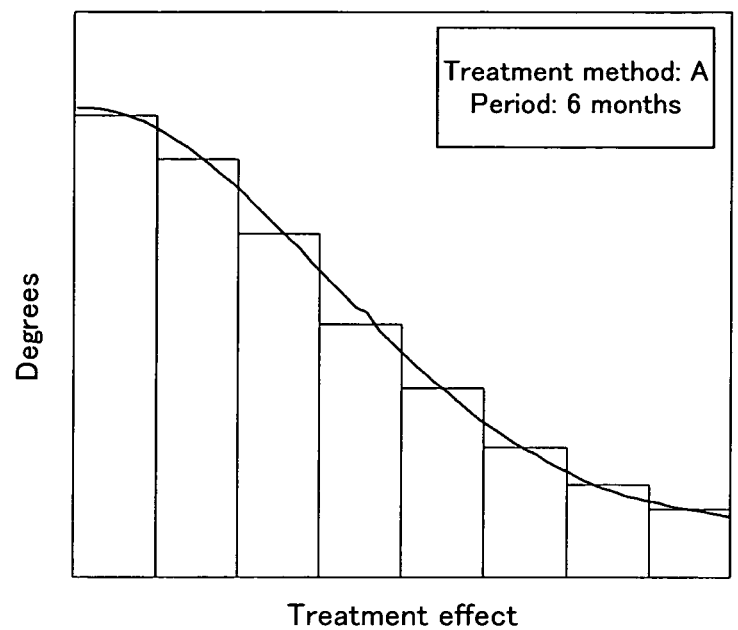
FIG. 20 shows an example of a template when different treatments are proposed for the same pathological condition information.
Figure 20:
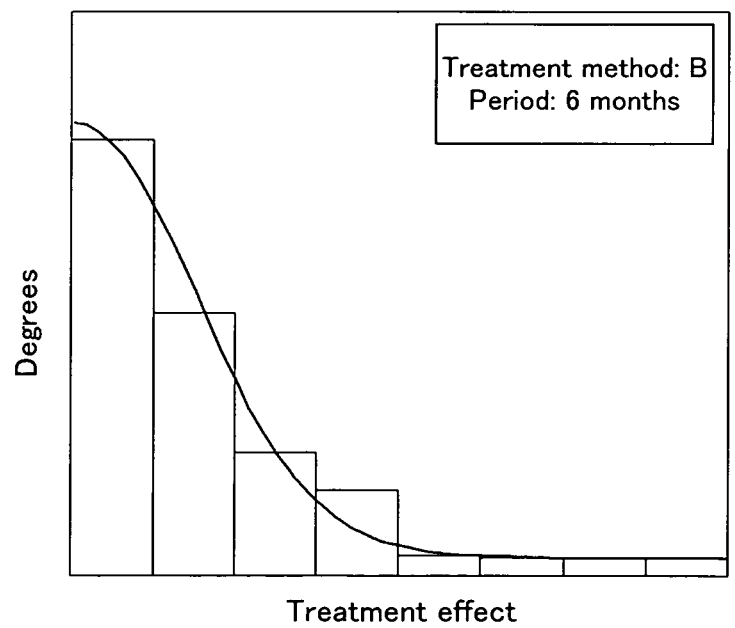

FIG. 20 shows an example of a template when different treatments are proposed for the same pathological condition information.

The previously mentioned finding is accomplished by using the pathological condition information obtained in step S2 as a query, and the CPU 110*a* determines whether or not pathological condition information similar to this pathological condition information is stored in the database DB. When similar pathological condition information is stored in the database DB, the CPU 110*a* obtains the treatment effects corresponding to this similar pathological condition information from the database DB, and displays the information on the system display 120 (step S5), whereupon the process ends. When similar pathological condition information is not stored in the database DB, the CPU 110*a* does not display a treatment effect, and the process ends.

The explanation above is a summary of the treatment effect prediction of the system of the present embodiment, and the main processes are described in detail below using diabetes as an example.

1. Obtaining Pathological Condition Information

Figure 5:
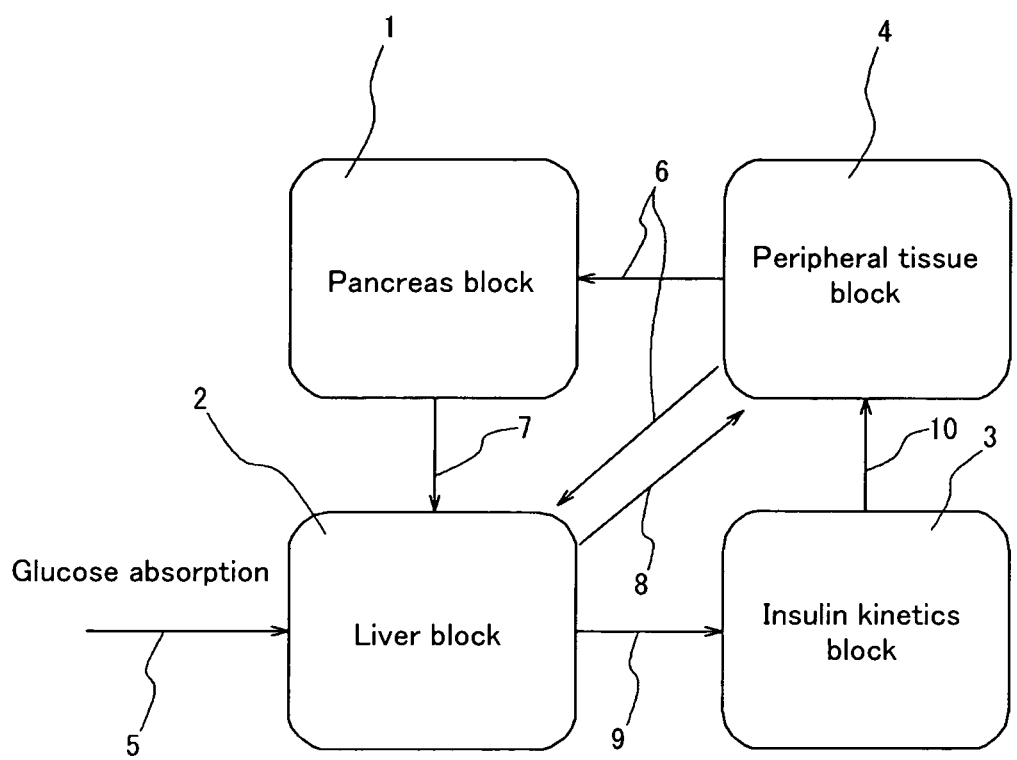
FIG. 5 is a function block diagram showing the overall structure of an example of a model of a living body used by the embodiment of the system of the present invention.

FIG. 5 is a function block diagram showing the overall structure of an example of a biological model used by the embodiment of the system of the present invention. As shown in FIG. 5, the biological model used by the system of the present embodiment is configured by a pancreas block 1, liver block 2, insulin kinetics block 3, and peripheral tissue block 4, and each of the block has an input and an output. That is, the pancreas block 1 has blood glucose concentration 6 as an input, and insulin secretion rate 7 as an output. The liver block 2 has digestive tract glucose absorption 5, blood sugar level 6 and insulin secretion rate as inputs, and net glucose release 8 and liver-processed insulin 9 as out puts. The insulin kinetics block 3 has liver-processed insulin 9 as an input, and peripheral tissue insulin concentration 10 as outputs. The peripheral tissue block 4 has net glucose release 8 and peripheral tissue insulin concentration 10 as inputs, and blood sugar level 6 as an output. The glucose absorption 5 is externally provided data; this function can be realized, for example, by inputting diagnostic data by a user using the input device 130. These function blocks 1 through 4 are realized when the CPU 110a executes the application program 140a.

As previously described, the means 300 for obtaining pathological condition information is configured by a biological model driving means 310 for simulating the behavior of a living body using a biological model realized by a mathematical model having a plurality of parameters of organ functions, parameter obtaining means 320 for obtaining parameters of a biological model appropriate to the patient based on diagnostic data input via the input means 200, and pathological condition information generating means 330 for generating pathological condition information of a patient based on parameters obtained by the parameter obtaining means 320, and the computer 100a is configured so as to function as a data base for storing specific operational expressions derived from mathematical models expressing organ functions, and as an operation means for calculating output values based on the values input to the biological model. The parameters suited to the patient can be determined using, for example, genetic algorithms methods, so as to obtain actual diagnostic values within a specific error range, and values obtained from simulation results.

Details of each block in the above example are described below. FBG and Ws respectively represent fasting blood glucose (FBG=BG(0)) and hypothetical weight; DVg and DVi respectively represent distribution capacity in glucose and distribution capacity volume in insulin.

The relationship of the inputs and outputs of the pancreas block 1 can be described using the differential equation (1) below. An equivalence of the differential equation (1) can be realized using the block diagram of FIG. 6. Differential equation (1)

$$dY/dt = \alpha\{Y(t) - \beta(BG(t)-h)\} \text{ (and, } BG(t) > h) = -\alpha Y(t) \text{ (and, } BG(t) <= h)$$

$$dX/dt = -M \cdot X(t) + Y(t)$$

$$SR(t) = M \cdot X(t)$$

Variables:
BG (t): Blood sugar level,
X (t): total insulin secretable from pancreas,
Y (t): Delivery speed of new insulin from glucose stimulation,
SR (t): Pancreatic insulin secretion rate parameters:
h: Glucose concentration threshold of stimulating insulin supply,
α: Tracking relative to glucose stimulation,
β: Sensitivity to glucose stimulation,
M: Secretion rate per unit concentration The blood sugar level 6 input in the pancreas block 1 in FIG. 5 corresponds to the BG(t), and the output insulin secretion rate 7 corresponds to the SR(t).

Figure 6:
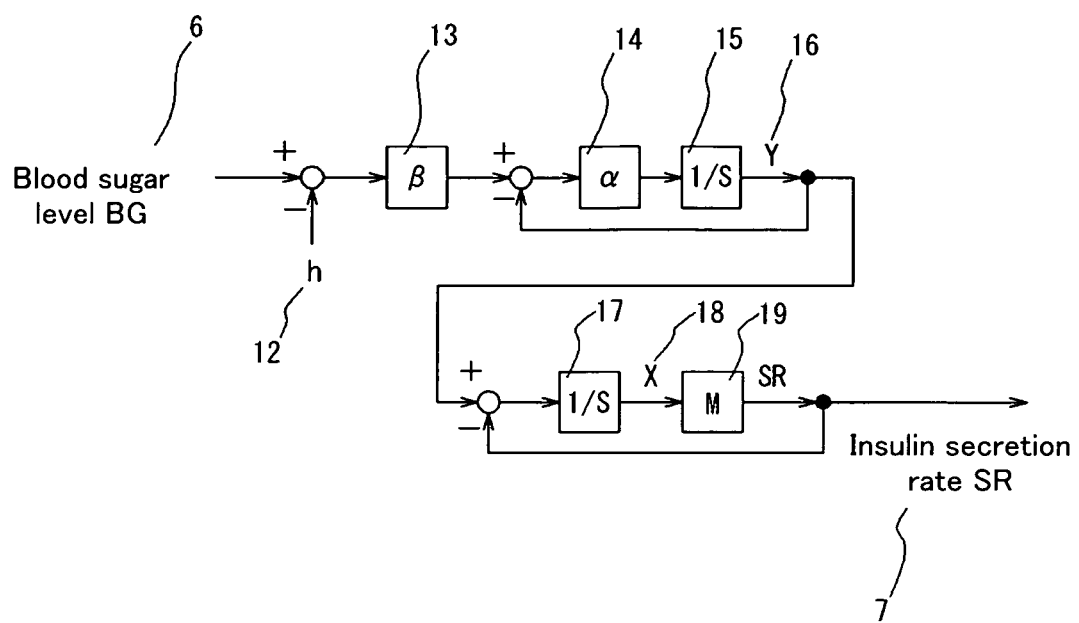
FIG. 6 is a block diagram showing the structure of a pancreas model in an example of the living body model used in an embodiment of the system of the present invention.

In the block diagram of FIG. 6, reference number 6 refers to the blood sugar level BG(t), 7 refers to the pancreatic insulin secretion rate SR(t), 12 refers to glucose concentration threshold h of stimulating insulin supply, 13 refers to sensitivity β to glucose stimulation, 14 refers to tracking a relative to glucose concentration, 15 refers to integral factor, 16 refers to delivery speed Y(t) of new insulin from glucose stimulation, 17 refers to integral factor, 18 refers to total insulin X(t) secretable from pancreas, and 19 refers to the secretion rate M per unit concentration.

The relationship of the inputs and outputs of the liver block 2 can be described using the differential equation (2) below.

Figure 7:
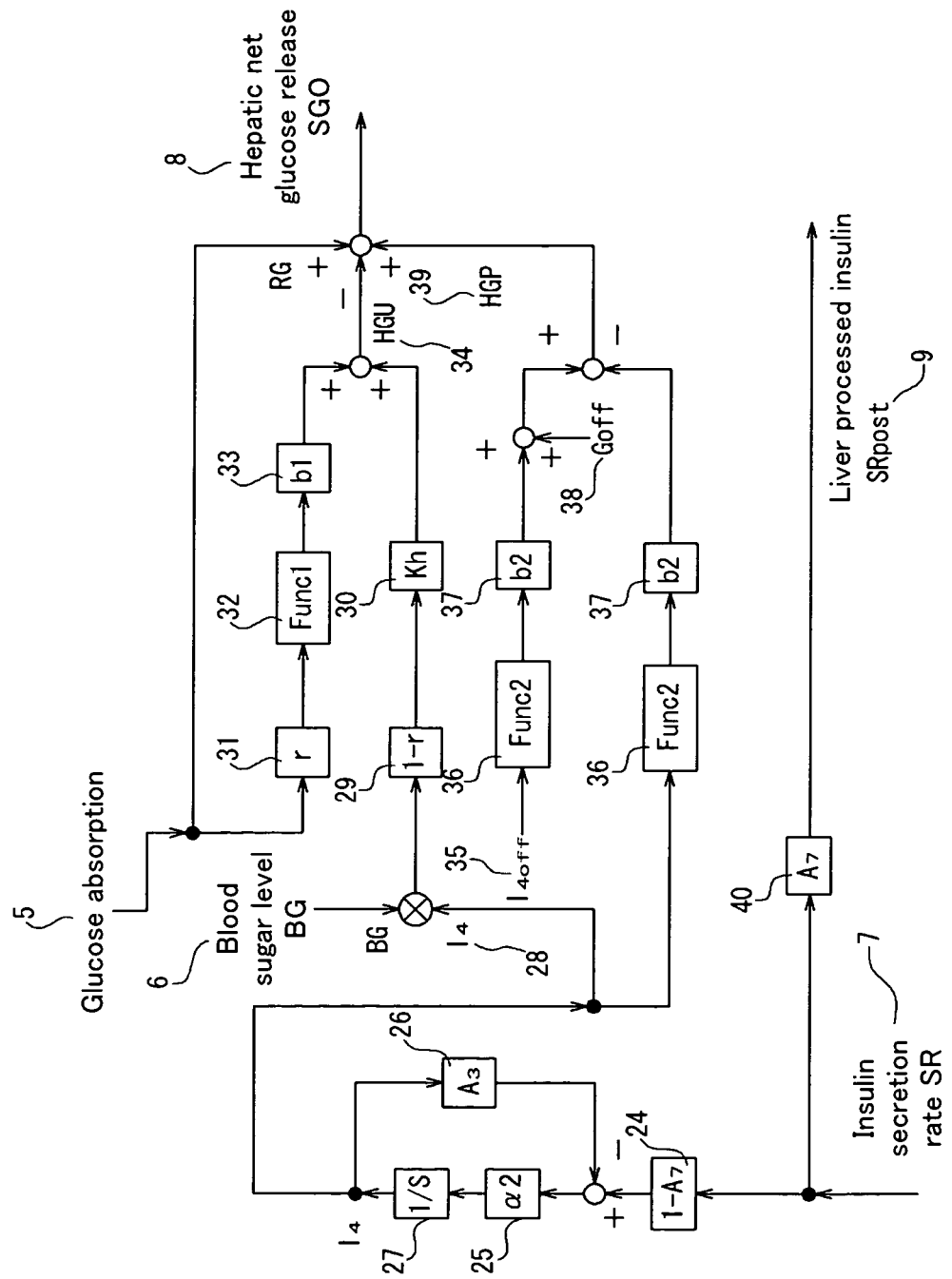
FIG. 7 is a block diagram showing the structure of a liver model in an example of the living body model used in an embodiment of the system of the present invention.

An equivalence of the differential equation (2) can be realized using the block diagram of FIG. 7. Differential equation (2)

$$dI_4(t)/dt = \alpha 2\{-A_3 I_4(t) + (1-A_7) \cdot SR(t)\}$$

$$Goff(FBG) =$$
$$\quad f1 \text{(and } FBG < f3) = f1 + f2 \cdot (FBG - f3) \text{(and } FBG >= f3)$$

$$\text{Func1}(FBG) = f4 - f5 \cdot (FBG - f6)$$

$$\text{Func2}(FBG) = f7/FBG$$

$$b1(I_4(t)) = f8\{1 + f9 \cdot I_4(t)\}$$

$$HGU(t) = r \cdot \text{Func1}(FBG) \cdot b1(I_4(t)) \cdot RG(t) +$$
$$\quad (1-r) \cdot Kh \cdot BG(t) \cdot I_4(t) \text{(and } HGU(t) >= 0\text{)}$$

$$HGP(t) = I_{4off} \cdot \text{Func2}(FBG) \cdot b2 + G_{off}(FBG) -$$
$$\quad I_4(t) \cdot \text{Func2}(FBG) \cdot b2 \text{ (and } HGP(t) >= 0$$

$$SGO(t) = RG(t) + HGP(t) - HGU(t)$$

$$SRpost(t) = A_7 SR(t)$$

Variables
BG (t): Blood sugar level,
SR (t): pancreatic insulin secretion rate,
SRpost (t): liver processed insulin,
RG (t): Digestive tract glucose absorption,
HGP (t): Hepatic glucose release,
HGU (t): Hepatic glucose uptake,
SGO (t): Net glucose from liver,
$I_4$ (t): Hepatic insulin concentration, parameters:
Kh: Hepatic glucose uptake rate per unit insulin and per unit glucose,
$A_7$: Hepatic insulin uptake rate,
Goff: Glucose release rate relative to basic metabolism,
b2: Adjustment of hepatic glucose release suppression rate,
r: Insulin independent hepatic glucose uptake distribution rate,
a2: hepatic insulin propagation rate,
$I_{4off}$: Insulin concentration threshold for suppressing hepatic glucose release,
Functions:
Goff (FBG): Glucose release rate relative to basic metabolism,
Func 1 (FBG): Hepatic glucose uptake rate from digestive tract glucose stimulation,
Func 2 (FBG): Hepatic glucose release suppression rate relative to insulin stimulation,
f1-f9: Constants used to realize three items above,
b1 ($I_4$ (t)): Adjustment item for hepatic glucose uptake rate,
Inputs to the liver block shown in FIG. 5 are digestive tract glucose absorption 5 corresponding to RG(t), blood sugar level 6 corresponding to BG(t), and pancreatic insulin secretion rate 7 corresponding to SR(t); and the outputs are net glucose from liver 8 corresponding to SGO(t), and liver processed insulin 9 corresponding to SRpost (t).

In the block diagram of FIG. 7, reference number 5 refers to the digestive tract glucose absorption RG(t), 6 refers to blood sugar level BG(t), 7 refers to pancreatic insulin secretion rate SR(t), 8 refers to net glucose from liver SGO(t), 9 refers to liver processed insulin SRpost (t), 24 refers to hepatic insulin passage rate (1-A7), 25 refers to hepatic insulin propagation rate α2, 26 refers to liver processed insulin distribution rate A3, 27 refers to integral factor, 28 refers to hepatic insulin concentration $I_4$ (t), 29 refers to insulin dependent hepatic glucose uptake distribution rate (1-r), 30 refers to hepatic glucose uptake rate Kh per unit insulin and per unit glucose, 31 refers to insulin independent hepatic glucose uptake distribution rate r, 32 refers to hepatic glucose uptake rate Func1 (FBG) from digestive tract glucose stimulation, 33 refers to adjustment itemb1 ($I_4(t)$) for hepatic glucose uptake rate, 34 refers to hepatic glucose uptake HGU (t), 35 refers to insulin concentration threshold $I_{40off}$ for suppressing hepatic glucose release, 36 refers to hepatic glucose release suppression rate Func2 (FBG) relative to insulin stimulation, 37 refers to adjustment b2 of hepatic glucose release suppression rate, 38 refers to glucose release rate Goff relative to basic metabolism, 39 refers to hepatic glucose release HGP (t), and 40 refers to hepatic insulin uptake rate $A_7$.

The relationship between the inputs and outputs of insulin kinetic secretion, can be described using differential equation (3) below. An equivalence of the differential equation (3) can be realized using the block diagram of FIG. 8. Differential equation (3)

$$dI(t)/dt = -A_3I_1(t) + A_5I_2(t) + A_4I_3(t) + SRpost(t)$$

$$dI_2(t)/dt = A_6I_1(t) - A_5I_2(t)$$

$$dI_3(t)/dt = A_2I_1(t) - A_1I_3(t)$$

Variables
SRpost (t): Liver processed insulin
$I_1$ (t): Blood insulin concentration
$I_2$ (t): Insulin concentration in insulin independent tissue
$I_3$ (t): Insulin concentration in peripheral tissue Parameters:
$A_1$: Insulin loss rate in peripheral tissue
$A_2$: Insulin distribution rate to peripheral tissue
$A_3$: Liver processed insulin distribution rate
$A_4$: Peripheral tissue processed insulin outflow rate
$A_5$: Insulin loss rate in insulin independent tissue
$A_6$: Insulin distribution rate to insulin independent tissue The liver processed insulin 9 input in the insulin kinetics block corresponds to SRpost (t), and the output peripheral tissue insulin concentration 10 corresponds to $I_3$ (t).

Figure 8:
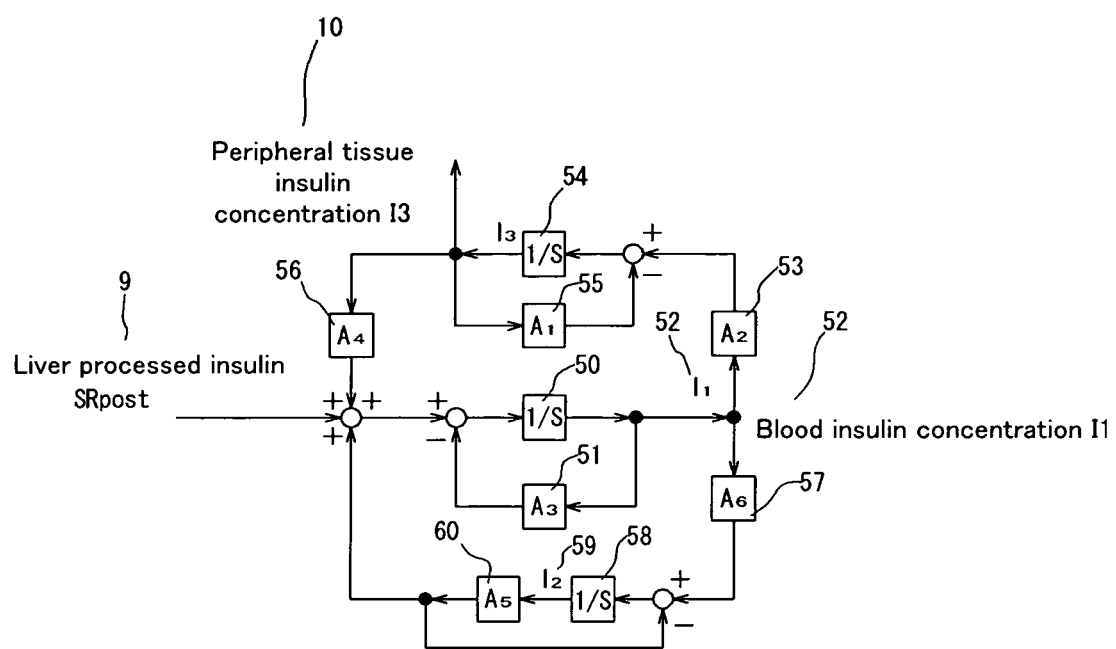
FIG. 8 is a block diagram showing the structure of an insulin kinetics model in the example of a living body mode used in the embodiment of the system of the present invention.

In the block diagram of FIG. 8, reference number 9 refers to liver processed insulin SRpost (t), 10 refers to insulin concentration $I_3$ (t) inperipheral tissue, 50 refers to integral factor, 51 refers to liver processed insulin distribution rate $A_3$, 52 refers to blood insulin concentration $I_1$ (t), 53 refers to insulin distribution rate $A_2$ to peripheral tissue, 54 refers to integral factor, 55 refers to insulin loss rate A1 in peripheral tissue, 56 refers to peripheral tissue processed insulin outflow rate $A_4$, 57 refers to insulin distribution rate $A_6$ to insulin independent tissue, 58 refers to integral factor, 59 refers to insulin concentration $I_2$ (t) in insulin independent tissue, 60 refers to insulin loss rate $A_5$ in insulin independent tissue.

Figure 9:
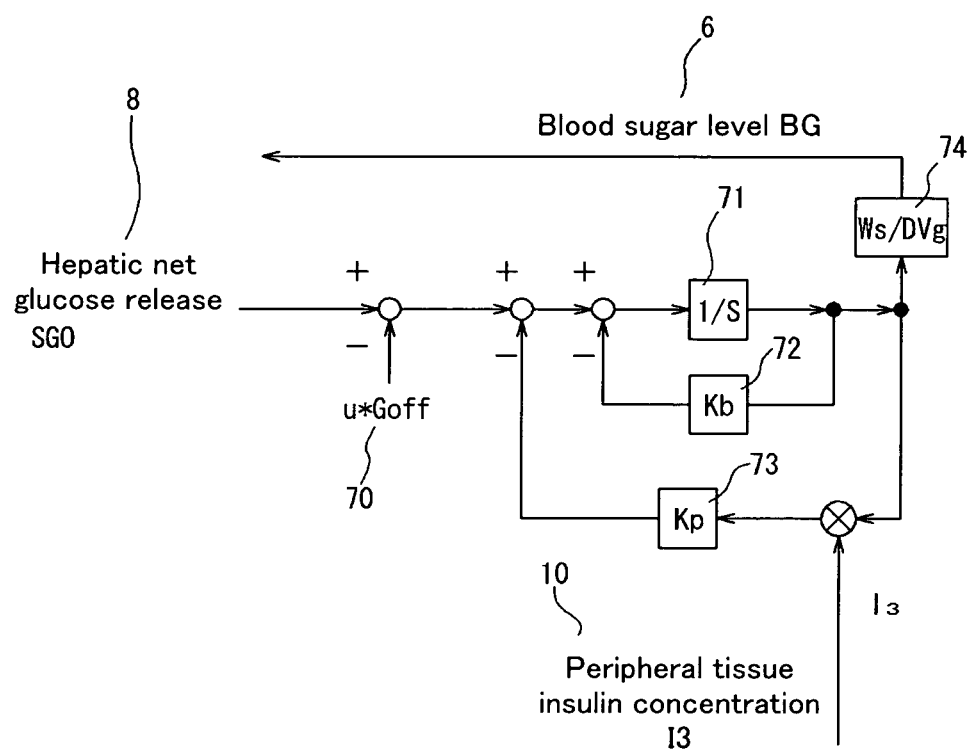
FIG. 9 is a block diagram showing the structure of a peripheral tissue model in an example of the living body model used in an embodiment of the system of the present invention.

The relationship of the inputs and outputs of the peripheral tissue block 4 can be described using the differential equation (4) below. An equivalence of the differential equation (4) can be realized using the block diagram of FIG. 9. Differential equation (4)

$$dBG'/dt = SGO(t) - u*Goff(FBG) - Kb \cdot BG'(t) - Kp \cdot I_3(t) \cdot BG'(t)$$

Variables
BG' (t): Blood sugar level (and BG[mg/dl], BG' [mg/kg])
SGO (t): Net glucose from liver,
$I_3$ (t): Peripheral tissue insulin concentration Parameters:
Kb: Insulin independent glucose consumption rate inperipheral tissue,
Kp: Insulin dependent glucose consumption rate in peripheral tissue per unit glucose and per unit insulin,
u: Percentage insulin independent glucose consumptionper-basic metabolism in glucose release rate relative to basic metabolism, Functions:

Goff (FBG): Glucose release rate relative to basic metabolism
f1-f3: Constants used to realize Goff The peripheral tissue insulin concentration 10 input to the peripheral tissue block 4 in FIG. 5 corresponds to $I_3$ (t), and the input net glucose 8 from the liver corresponds to SGO (t), and the output blood sugar level 6 corresponds to BG (t).

In the block diagram 9, reference number 6 refers to blood sugar level BG (t), 8 refers to the net glucose from the liver SGO (t), 10 refers to peripheral tissue insulin concentration $I_3$ (t), 70 refers to insulin independent glucose consumption rate relative to basic metabolism u*Goff (FBG), 71 refers to integral factor, 72 refers to insulin independent glucose consumption rate in peripheral tissue Kb, 73 refers to insulin dependent glucose consumption rate Kp in peripheral tissue per unit insulin and per unit glucose and per unit insulin, 74 refers to unit conversion constant Ws/Dvg.

As shown in FIG. 5, since the inputs and outputs of this block are mutually connected, the time series change of the blood sugar level and insulin concentration can be calculated based on mathematical expressions by using the glucose absorption 5 from the digestive tract, and a simulation can be created. The successively calculated blood sugar levels and insulin concentrations can be displayed on the display 120. Thus, the result of the modeled organs can be easily verified by the user.

The calculations of the differential equations can be accomplished, for example, using E-Cell (Keio University published software), or MATLAB (Mathworks, Inc.), although other calculation systems may also be used.

Obtaining Parameter Values

Parameter values can be obtained (generated) by, for example, the parameter set estimating process described below.

Figure 23:
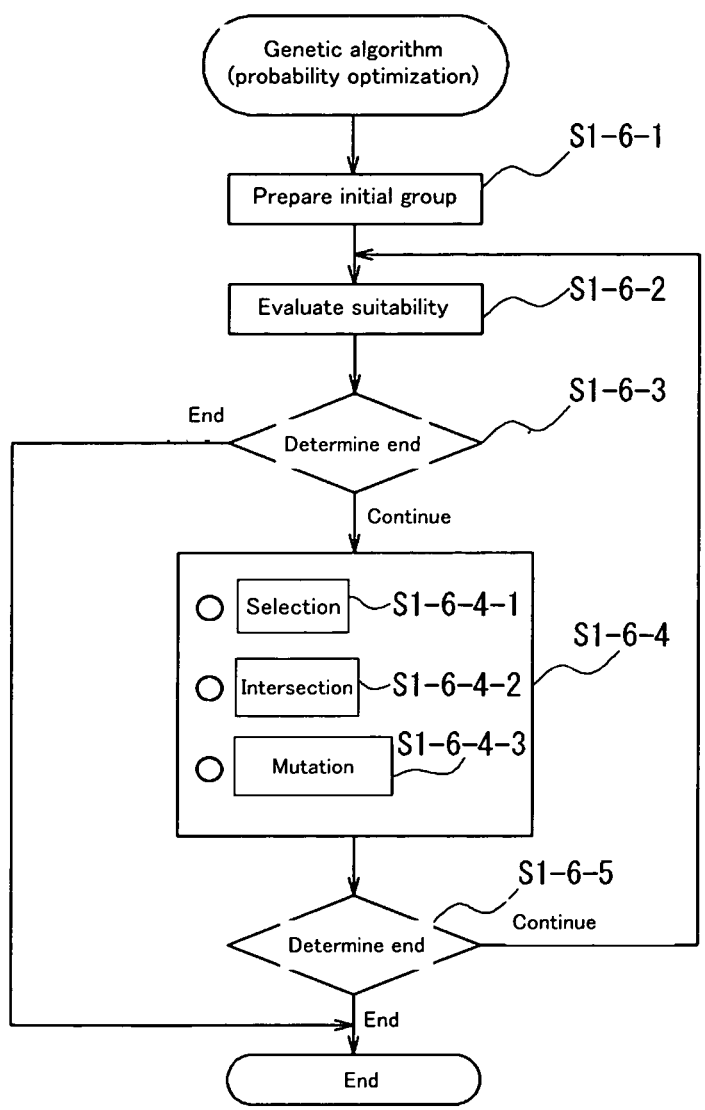
FIG. 23 shows the parameter set estimating process using a genetic algorithm.

FIG. 23 shows a parameter set estimating process using a genetic algorithm (hereinafter referred to simply as "GA") As shown in FIG. 23, the generation of parameter values by GA is accomplished by performing a process for generating a parameter set initial group (step S1-6-1), suitability evaluation process (step S1-6-2), selection/intersection/mutation-process (step S1-6-4), and end determination process (steps S1-6-3, S1-6-5).

The algorithm of FIG. 23 is described below.
[Initial Group Creation: Step S1-6-1]

The present system has biological model parameters with information in a search range, as shown in Table 1 below. The search range of table 1 is a range of values obtained from humans, and the search range of Table 1 is referred to as a "basic search range" below.

The present system has a function for auto-generating a parameter set PS in real time by generated random numbers in a range between minimum and maximum values in Table 1 for each parameter. The parameter set PS thus obtained is referred to as an "individual" set.

TABLE 1

| Fixed Parameter Search Range | | | | |
|---|---|---|---|---|
| | Parameter | Min Value | Max Value | Units |
| Pancreas | h | 21.06 | 526.5 | [mg/dl] |
| | α | 0.00304 | 0.684 | [1/min] |
| | β | 0.0751168 | 338.0256 | [(μU/ml) · (dl/mg) · (1/min)] |
| | M | 0.02 | 1 | [1/min] |
| | X(0) | 67.28 | 15138 | [μU/ml] |
| | Y(0) | 0.88 | 198 | [(μU/ml) · (1/min)] |

TABLE 1-continued

Fixed Parameter Search Range

| | Parameter | Min Value | Max Value | Units |
|---|---|---|---|---|
| Insulin Kinetics | $A_1$ | 0.005 | 0.075 | [1/min] |
| | $A_2$ | 0.0084 | 0.126 | [1/min] |
| | $A_3$ | 0.087 | 1.305 | [1/min] |
| | $A_4$ | 0.004 | 0.06 | [1/min] |
| | $A_5$ | 0.0788 | 1.182 | [1/min] |
| | $A_6$ | 0.0284 | 0.426 | [1/min] |
| Peripheral tissue | Kb | 0.0018 | 0.027 | [1/min] |
| | Kp | 6.66667E−07 | 0.001 | [(ml/μU) · (1/min)] |
| | u | 0.12 | 1.8 | |
| Liver | $A_7$ | 0.094 | 1.41 | |
| | Kh | 0.00000924 | 0.0001386 | [(ml/μU) · (1/min) · (dl/kg)] |
| | b1 | 0.18 | 2.7 | |
| | b2 | 0.22 | 3.3 | |
| | r | 0.196 | 1 | |
| | α2 | 0.00304 | 0.684 | |
| | $I_{4off}$ | 1 | 15 | [μU/ml] |

An initial group of several (for example, ten) parameter sets PS can be generated by repeating a process by CPU 110*a* for generating random numbers for each parameter within the search range of Table 1.

[Suitability Evaluation: Step S1-6-2]

The present system (CPU 110*a*) performs suitability evaluation of the generated individual sets, and selects and extracts part of the individual set PS from among the individual sets PS in the groups.

The suitability evaluation uses the time series data of actually measured OGTT as a reference. The actual measurement data (biological response) used for a reference are data which are reproducible as output of the biological model by the present system, and the individual sets have high suitability to the actual measurement values if the response obtained is similar to the reference in the biological model to which the generated parameter set is applied.

The suitability evaluation of the generated parameters is accomplished by determining the degree of similarity (suitability) between the generated model output (blood sugar data and insulin concentration data) to which the generated parameters are applied, and the reference (OGTT glucose data and OGTT insulin data).

[Selection: Step S1-6-4-1]

Then, the present system (CPU 110*a*) selects part (for example 4 individual sets) from among the (initial) group, as a [parent] based on, for example, the highest degree of suitability, a predetermined selection standard. The selection standard is not limited to [high suitability sets] since later generation [offspring] can be expected to have high suitability, such that the standard may include part of a low suitability [parent].

[Intersection: Step S1-6-4-2]

The present system (CPU 110*a*) generates, in the sequence below, two new [offspring] from the individual set group selected as the [parent] by the [selection]

First, (1) two optional individual sets are selected from the selected individual set group. Next, (2) the number of intersections of the analogous individual sets (number of parameters as intersection object) is determined. Intersection probability is multiplied by R (range of 0 to 1), and the number of intersection is determined by the following equation.

Number of intersections=[XR×number of parameters belonging to 1 individual set]

The brackets [ ] is a Gaussian symbol. (Example) [3.14]=3

Then, (3) The intersection points are determined. The intersection points are determined by randomly generating integer value, between 1 and the number of the parameter([22] in the case of Table 1), the number of "intersection" times.

Finally, (4) new individual sets are generated. Specifically, two new individual sets are generated by converting the parameters of the intersecting points determined in (3) from the two individual sets selected in (1).

A new individual [offspring] is generated from several (six in this example) diminished by the [selection] by repeating the processes (1) through (4).

[Mutation: Step S1-6-4-3]

Finally, the present system (CPU 110*a*) changes each parameter of each individual set in the sequence below via a mutation probability (range 0 to 1) relative to all individual sets of the new group.

For example, the mutation process generates a random number R in the range 0 to 1 from the parameters of a particular individual set, and generates random numbers within the search field shown in Table 2 when R<MR, and replaces the original parameter value. An identical process is performed for all parameters of all individual sets.

[End Condition Determining Process: Steps S1-6-3, S1-6-5]

Although the processes of steps S1-6-2 to A1-6-4 are repeated, as shown in FIG. 23, the CPU 110*a* ends the GA process and individual set (parameter set) of optimum suitability among the groups as the estimation result when the result of the suitability evaluation process in step S1-6-2 is the most suitable individual set above a predetermined standard among the current group.

Furthermore, when the number of repetitions of the processes from step S1-6-2 to S1-6-4 exceeds a certain number, the CPU 110*a* ends the GA process, and the individual set (parameter set) with the optimum suitability in the group is set as the estimation result (step S1-6-5). The number of repetitions for the end condition is set at, for example, 300.

Although the parameters can be determined by the biological model parameter set estimating process above, the organs of the patient can be appropriately simulated since the biological model can generate output approaching the input OGTT time series data.

Simulation Examples

An example of the simulation of a time series change of blood sugar level, blood insulin concentration, hepatic glucose uptake, and hepatic glucose release using the present system follows. In this example, the values of Table 2 are used as examples of the block parameters.

TABLE 2

| | Parameter | Value | Units |
|---|---|---|---|
| Pancreas | h | 92.43 | [mg/dl] |
| | α | 0.228 | [1/min] |
| | β | 0.357 | [(μU/ml) · (dl/mg) · (1/min)] |
| | M | 1 | [1/min] |
| Insulin Kinetics | $A_1$ | 0.025 | [1/min] |
| | $A_2$ | 0.042 | [1/min] |
| | $A_3$ | 0.435 | [1/min] |
| | $A_4$ | 0.02 | [1/min] |
| | $A_5$ | 0.394 | [1/min] |
| | $A_6$ | 0.142 | [1/min] |
| Peripheral tissue | Kb | 0.009 | [1/min] |
| | Kp | 5.28E−05 | [(ml/μU) · (1/min)] |
| | u | 0.6 | |
| Liver | $A_7$ | 0.47 | |
| | Kh | 0.0000462 | [(ml/μU) · (1/min) · (dl/kg)] |
| | b2 | 1.1 | |
| | r | 0.98 | |
| | α2 | 0.228 | |
| | $I_{4off}$ | 5 | [μU/ml] |

The values of Table 3 are used as the initial values of variable in the calculation of the differential equation.

TABLE 3

|  | | Initial Value | Value | Units |
|---|---|---|---|---|
| Pancreas | | $X(0)$ | 336.4 | [μU/ml] |
| | | $Y(0)$ | 4.4 | [(μU/ml) · (1/min)] |
| Insulin Kinetics | | $I_1(0)$ | 8 | (μU/ml) |
| | | $I_2(0)$ | $I_1(0) * (A_2/A_1)$ | [μU/ml] |
| | | $I_3(0)$ | $I_1(0) * (A_6/A_5)$ | [μU/ml] |
| | | $I_4(0)$ | 4 | [μU/ml] |
| Liver | | FBG | 115 | [mg/dl] |

Furthermore, the values of Table 4 are used as examples of standard values in the standardization of the present example.

TABLE 4

| | Constant | Value | Units |
|---|---|---|---|
| Function | f1 | 1.8 | [(mg/kg) · (1/min)] |
| | f2 | 0.02 | [(dl/kg) · (1/min)] |
| | f3 | 140 | [mg/dl] |
| | f4 | 0.525 | |
| | f5 | 0.005 | [dl/mg] |
| | f6 | 80 | [mg/dl] |
| | f7 | 13.2 | [(ml/μU) · (mg/dl) · (mg/kg) · (1/min)] |
| | f8 | 0.9 | |
| | f9 | 0.0001 | [ml/μU] |
| Standard | Ws | 70 | [kg] |
| | DVg | 154 | [dl] |
| | DVi | 3.52 | [l] |

Figure 10:
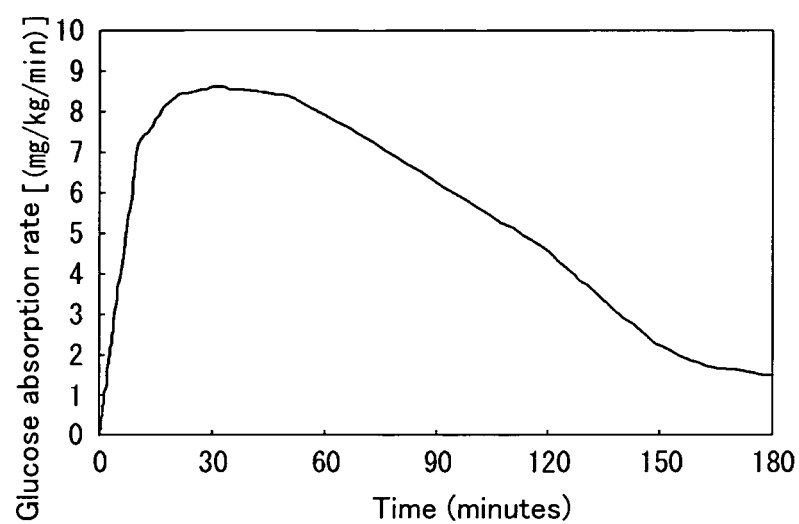
FIG. 10 is a graph showing the glucose absorption speed used as an input in the example of the present invention.

The digestive tract glucose absorption speed uses the values shown in FIG. 10.

Figure 11:
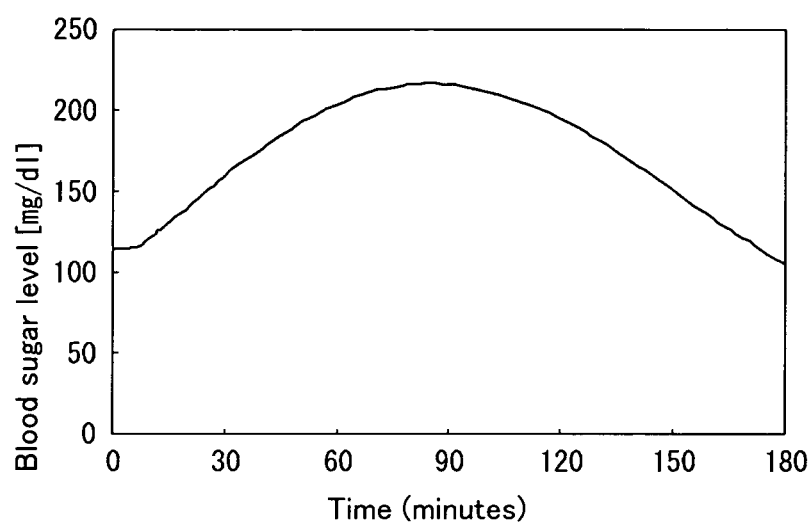
FIG. 11 is a graph showing simulated blood sugar levels in an example of the present invention.
Figure 12:
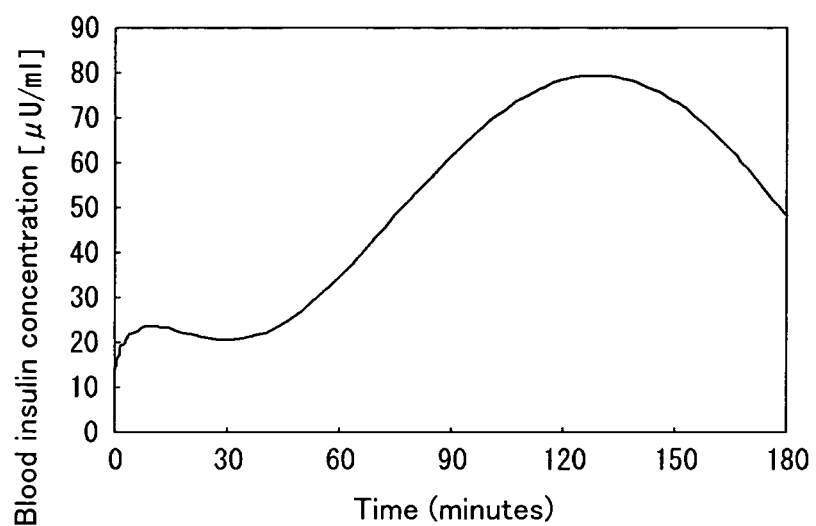
FIG. 12 is a graph showing simulated blood insulin concentration in an example of the present invention.
Figure 13:
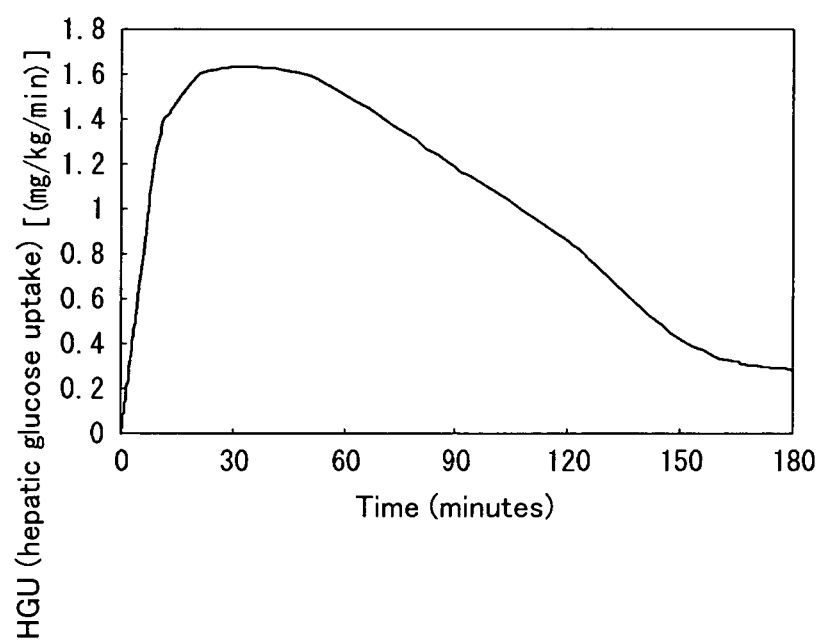
FIG. 13 is a graph showing simulated hepatic glucose uptake in an example of the present invention.
Figure 14:
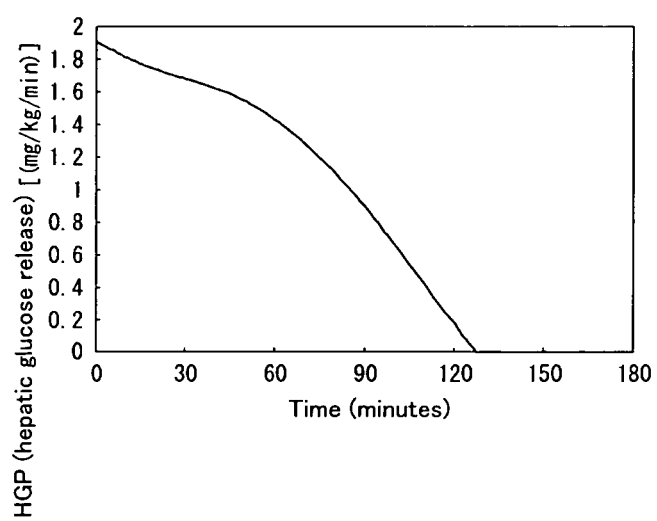
FIG. 14 is a graph showing simulated hepatic glucose release in an example of the present invention.
Figure 15:
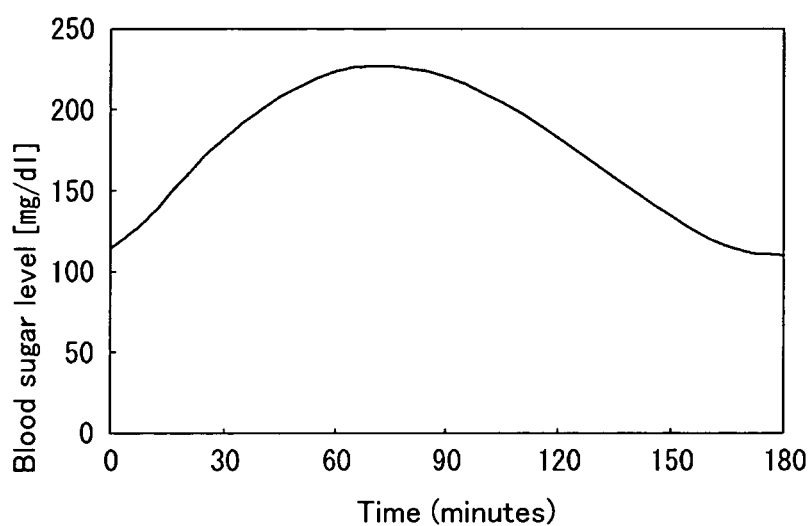
FIG. 15 is a graph showing reference blood sugar levels.
Figure 16:
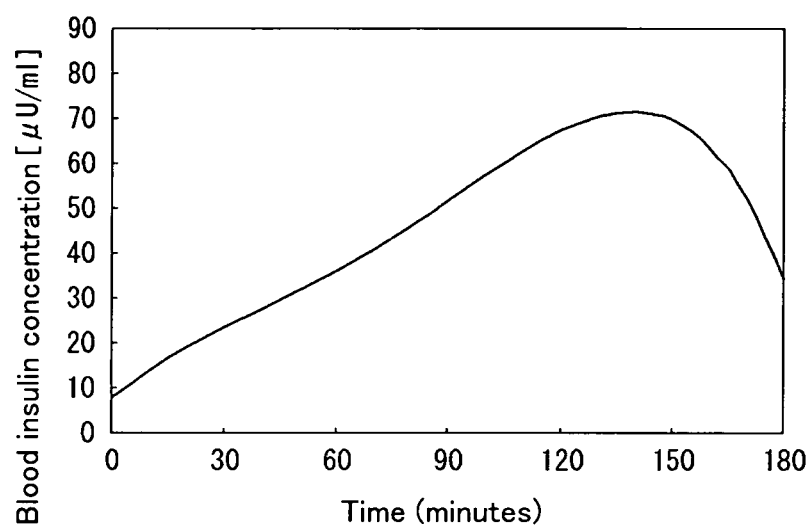
FIG. 16 is a graph showing reference blood insulin concentrations.
Figure 17:
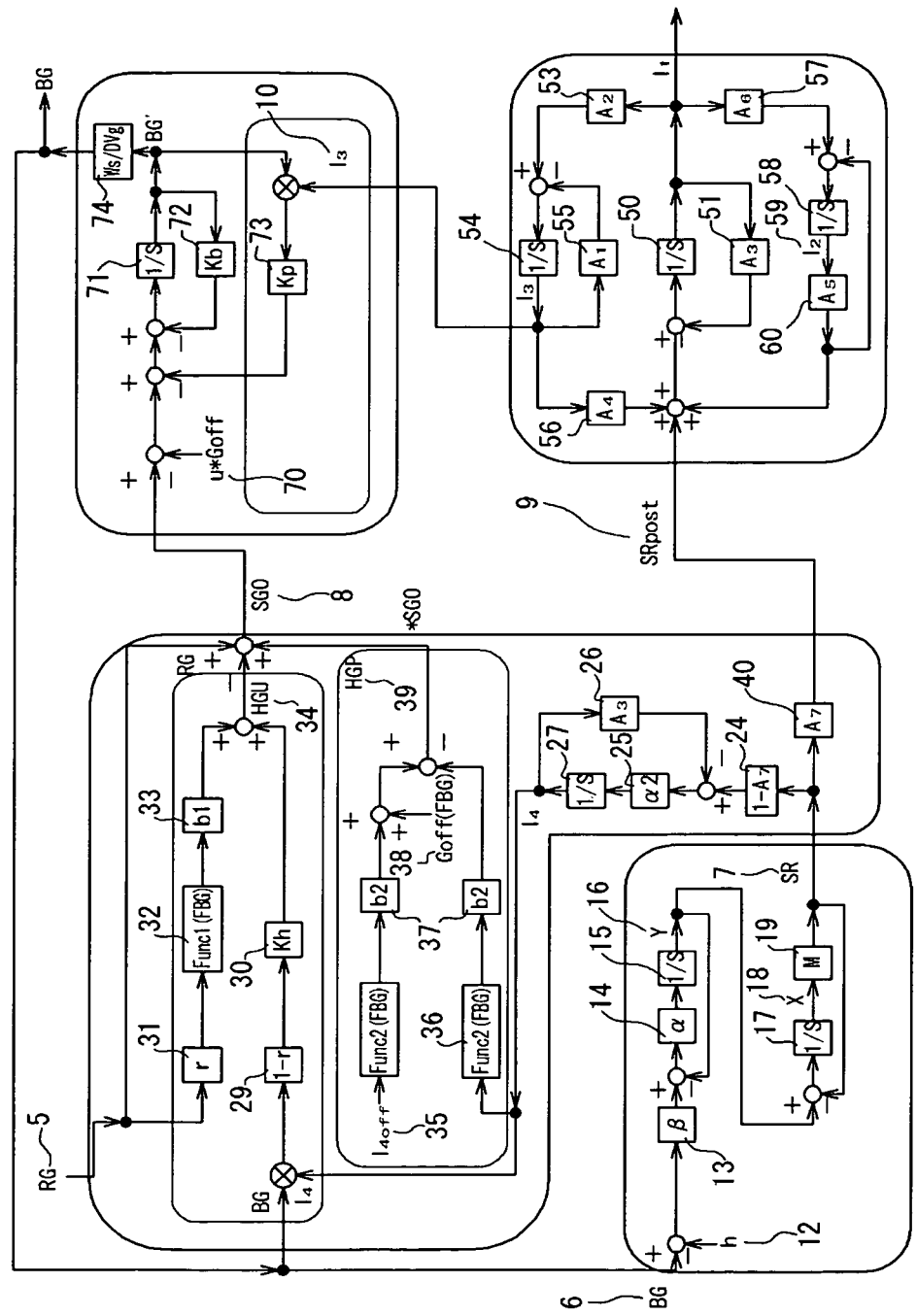
FIG. 17 shows the overall structure of an example of a living body model used in the present invention.

The simulation results under the above conditions are blood sugar 6 time series change shown in FIG. 11, blood insulin concentration 49 time series change shown in FIG. 12, hepatic glucose uptake time series change shown in FIG. 13, and hepatic glucose release time series change shown in FIG. 14. Furthermore, the reference blood sugar levels are shown in FIG. 15, and the reference blood insulin concentrations are shown ion FIG. 16.

Thus, using the present system the change over time of the blood sugar level due to glucose absorption, blood insulin concentration, hepatic glucose uptake, and hepatic glucose release can be reproduced in a form closely approaching a biological change. Furthermore, the medical significance can be readily appreciated since the model used in the present system includes, as structural elements, function blocks respectively corresponding to the pancreas, liver, insulin kinetics, and peripheral tissue that control the blood sugar level.

2. Database for Treatment Effect Prediction

Expected treatment effects are stored in the database DB for treatment effect prediction using the pathological condition information and treatment method as keys.

Pathological condition information is represented by a one or a plurality of numerical values indicating the condition of the patient, for example, insulin secretory defect score, peripheral insulin resistance score, hepatic glucose uptake score and hepatic glucose release score can be calculated by, for example, the pathological condition information obtaining means 300, and used as the pathological condition information (narrow definition of pathological condition information). Furthermore, in addition to these scores, age, sex, weight and other codable patient attributes may also be used a pathological condition information (broad definition of pathological condition information).

As previously described, the treatment methods are coded combinations of treatment methods obtained from patients, in the case of diabetes, for example, characteristics codes may be allocated to dietary treatments, exercise treatments, sulfonyl urea, fast-acting insulin secretory accelerator, insulin resistance enhancer, glucose absorption inhibitor, manufactured insulin, and the like individually and in a plurality of combinations.

Treatment effects are the amount of improvement of a pathological condition expected by a treatment and are represented by numeric values; in the case of diabetes, for example, the amount of decrease in the blood sugar level expected, combined with the probability of that decrease can be used in a list.

Tables 5 through 7 show examples of treatment effects, codes of treatment methods, and pathological conditions.

TABLE 5

| Peripheral insulin resistance | Impaired hepatic glucose uptake | Excessive hepatic glucose release | Insulin secretory defect | Age | Sex | Weight |
|---|---|---|---|---|---|---|
| 10 | 40 | 40 | 40 | 65 | 1 | 75 |
| 10 | 40 | 40 | 40 | 65 | 2 | 60 |
| 40 | 60 | 60 | 80 | 65 | 1 | 75 |
| 40 | 60 | 60 | 80 | 65 | 2 | 60 |
| 60 | 20 | 20 | 60 | 70 | 1 | 75 |
| 60 | 20 | 20 | 60 | 70 | 2 | 60 |

TABLE 6

| Diet | Exercise | Insulin secretion accelerator | Insulin resistance enhancer | Glucose release inhibitor | Glucose absorption inhibitor | Insulin | Method No. |
|---|---|---|---|---|---|---|---|
| No | No | No | No | No | No | No | 0 |
| Yes | Yes | No | No | No | Yes | No | 1 |
| Yes | Yes | Yes | No | No | Yes | No | 2 |
| Yes | Yes | No | Yes | No | Yes | No | 3 |
| Yes | Yes | Yes | Yes | No | Yes | No | 4 |
| Yes | Yes | No | Yes | Yes | Yes | No | 5 |
| Yes | Yes | Yes | Yes | Yes | Yes | No | 6 |

TABLE 7

| | Amt drop in Blood sugar level | | | | | | |
|---|---|---|---|---|---|---|---|
| | Under 20 | 20–39 | 40–59 | 60–79 | 80–99 | 100–119 | 120 and above |
| Probability | 0.25 | 0.30 | 0.20 | 0.10 | 0.05 | 0.05 | 0.05 |

Pathological condition information is stored in a relational database. Tables 8 and 9 shows examples; Table 8 has fields of insulin secretory defect, peripheral insulin resistance, impaired hepatic glucose uptake, excessive hepatic glucose release, age, sex, weight, treatment method, and treatment effect Number. Table 9 has fields of treatment effect number, amount of blood sugar decrease, and probability.

TABLE 8

| Peripheral insulin resistance | Impaired hepatic glucose uptake | Excessive hepatic glucose release | Insulin secretory defect | Age | Sex | Weight | Treatment method | Treatment effect No. |
|---|---|---|---|---|---|---|---|---|
| 10 | 40 | 40 | 40 | 65 | 1 | 75 | 3 | 1 |
| 10 | 40 | 40 | 40 | 65 | 2 | 60 | 3 | 2 |
| 40 | 60 | 60 | 80 | 65 | 1 | 75 | 2 | 3 |
| 40 | 60 | 60 | 80 | 65 | 2 | 60 | 2 | 4 |
| 60 | 20 | 20 | 60 | 70 | 1 | 75 | 2 | 5 |
| 60 | 20 | 20 | 60 | 70 | 2 | 60 | 2 | 6 |

TABLE 9

| Treatment effect No. | Amt blood sugar decrease | Probability |
|---|---|---|
| 1 | 0–19 | 0.25 |
| 1 | 20–39 | 0.30 |
| 1 | 40–59 | 0.20 |
| 1 | 60–79 | 0.10 |
| 1 | 80–99 | 0.05 |
| 1 | 100–119 | 0.05 |
| 1 | 120 and over | 0.05 |
| 2 | 0–19 | 0.25 |
| 2 | 20–39 | 0.25 |
| 2 | 40–59 | 0.50 |
| 2 | 60–79 | 0.0 |
| 2 | 80–99 | 0.0 |
| 2 | 100–119 | 0.0 |
| 2 | 120 and over | 0.0 |

The data stored in Table 9, can be created, for example, described below.

(1) Step 1: Building Treatment Result Database

The pre-treatment pathological conditions of a plurality of patients is stored in a treatment result database as pathological condition information. The treatment methods used from the start of treatment are codified and stored in the same database. The treatment effects are stored after treatment.

An example of a relational database storing treatment results is shown in table 10. Table 10 has the fields of patient ID, insulin secretory defect, peripheral insulin resistance, impaired hepatic glucose uptake, excessive hepatic glucose release, age, sex, weight, treatment method, and treatment effect.

TABLE 10

| Patient ID | Peripheral insulin resistance | Impaired hepatic glucose uptake | Excessive Hepatic glucose release | Insulin secretory defect | Age | Sex | Weight | Treatment method | Treatment effect |
|---|---|---|---|---|---|---|---|---|---|
| 1 | 20 | 40 | 40 | 60 | 65 | 1 | 75 | 3 | 10 |
| 2 | 25 | 45 | 45 | 60 | 65 | 1 | 74 | 3 | 40 |

TABLE 10-continued

| Patient ID | Peripheral insulin resistance | Impaired hepatic glucose uptake | Excessive Hepatic glucose release | Insulin secretory defect | Age | Sex | Weight | Treatment method | Treatment effect |
|---|---|---|---|---|---|---|---|---|---|
| 3 | 20 | 55 | 55 | 90 | 65 | 1 | 76 | 2 | 10 |
| 4 | 20 | 40 | 40 | 90 | 65 | 1 | 80 | 2 | 60 |
| 5 | 25 | 45 | 45 | 55 | 70 | 1 | 79 | 3 | 40 |
| 6 | 15 | 35 | 35 | 65 | 70 | 1 | 82 | 3 | 35 |

(2) Step 2: Calculate Treatment Effect From Treatment Result Database

The records of Table 10 are classified as pathological condition information, and a probability distribution of the treatment effects is prepared.

For example, from Table 10, the peripheral insulin resistance scores are 10 to 30, impaired hepatic glucose uptake score are 30 to 50, excessive hepatic glucose release scores are 30 to 50, insulin secretory defect scores are 50 to 70, age scores are 60 to 70, sex score is 1, weight scores are 70 to 90, and structured query language (SQL), terminology is used to obtain codes of three treatment methods. SELECT treatment result FROM Table 10 WHERE peripheral insulin resistance BETWEEN 10 AND 30 AND impaired hepatic glucose uptake BETWEEN 30 and 50 AND excessive hepatic glucose release BETWEEN 30 and 50, AND insulin secretory defect BETWEEN 50 and 70, AND age BETWEEN 60 AND 70 AND sex=1 AND weight BETWEEN 70 AND 90 AND treatment methods=3. In this example, the records of the treatment effect field are output for patient IDs 1, 2, 5, and 6.

Output treatment effect: 10, 40, 40, 50

A treatment effect probability distribution is prepared from this output. At this time, the width of the gradient values is optionally determined. For example, if there is a decrease in blood sugar level, the width of each gradient can be set at 20 mg/dl.

In this case, the probability distribution according to the example of treatment effect is 0.25 for a blood sugar reduction of under 20, 0.25 for reduction of 20 to 39, and 0.5 for reduction of 40 to 59.

Median values of each field used when extracting codes, for example, are used as representative values of pathological condition information corresponding to treatment effect. That is, in the example, the peripheral insulin resistance score 20, impaired hepatic glucose uptake score 40, excessive hepatic glucose release score 40, insulin secretory defect score 60, age 60, sex 1, weight 75, and treatment method 3 can be set as representative values of pathological condition information.

Table 11 through 12 show examples of representative values of treatment effects and corresponding pathological condition information.

TABLE 11

| | Blood sugar level decrease | | | | | | |
|---|---|---|---|---|---|---|---|
| | Under 20 | 20–39 | 40–59 | 60–79 | 80–99 | 100–119 | 120 and over |
| Probability | 0.25 | 0.25 | 0.5 | 0 | 0 | 0 | 0 |

TABLE 12

| Peripheral insulin resistance | Impaired hepatic glucose uptake | Excessive Hepatic glucose release | Insulin secretory defect | Age | Sex | Weight | Treatment method |
|---|---|---|---|---|---|---|---|
| 20 | 40 | 40 | 60 | 65 | 1 | 75 | 3 |

(3) Storing Treatment Effects in the Database

The treatment effect obtained in step 2 is stored in Tables 8 and 9. The treatment effect is designated EE, and the representative value of the pathological condition information is designated P.

First, a non-repeated uniform number Ni is obtained. Then, a record R configured by the representative number P and Ni of the pathological condition profile in Table 8 is added. Finally, each gradient value of Ni and treatment effect EE and their probabilities are added to Table 9.

3. Database Search

Figure 21:
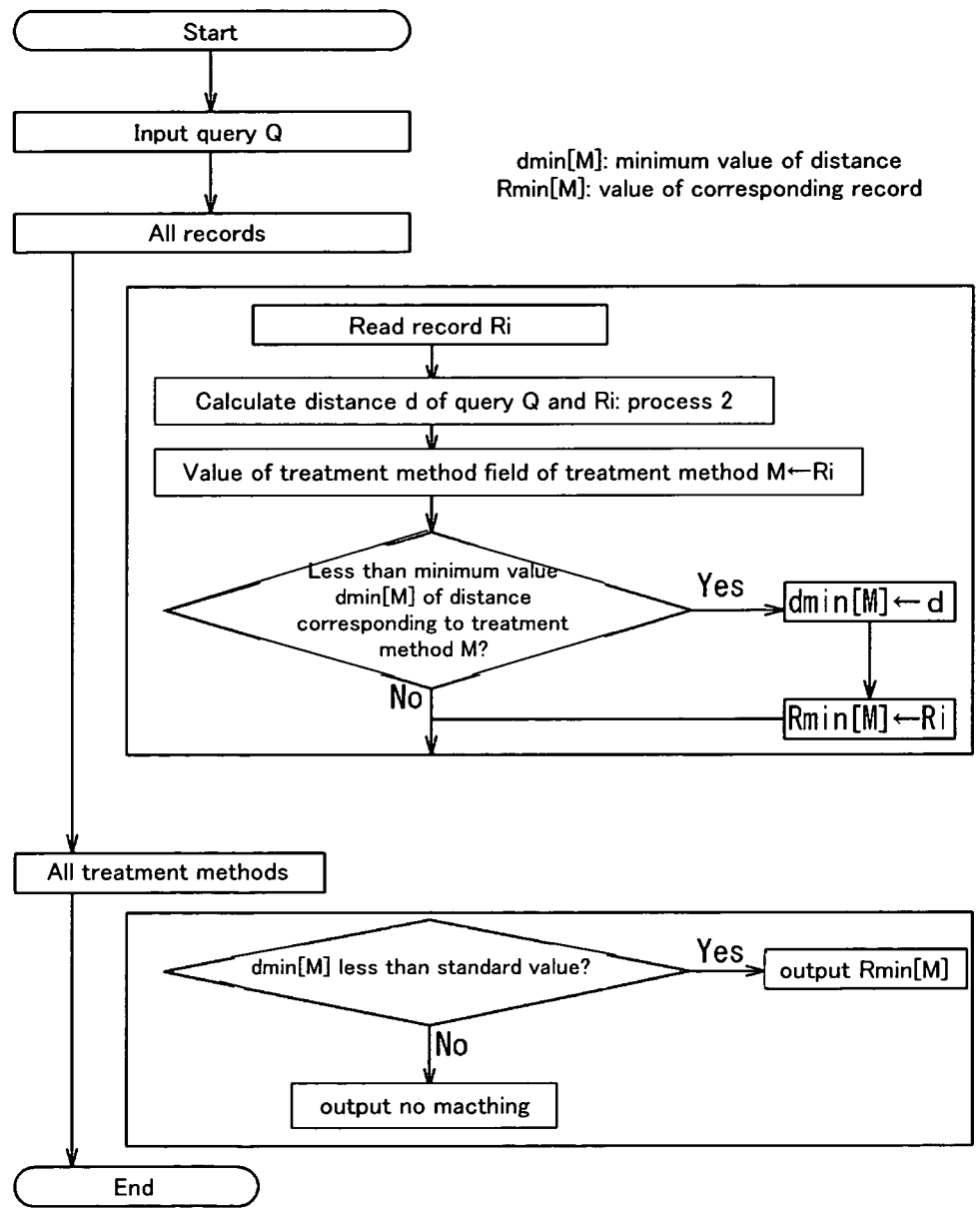
FIG. 21 shows an example of a method for searching a database using the pathological condition information of a specific patient in a query.

The database is then queried, for example, in the manner described below for pathological condition information of a specific patient obtained by the pathological condition information obtaining means. That is, as shown in FIG. 21, records satisfying a standard of similarity (degree of similarity), that is, most similar, are output for pathological condition information of a specific patient.

More specifically, pathological condition information (query Q) of a specific patient obtained by the pathological condition information obtaining means is input (step S11). Then, all records Ri are sequentially read from the database DB (step S12), and the distance d of the query Q and record Ri is calculated by the CPU 110a (step S13).

The calculation of the distance d can be accomplished, for example, as described below. The initial value of a minimum distance value dmin [M] corresponding to a certain treatment method is set at infinity ($\infty$).

First, di=infinity when the the [sex] fields of Q and Ri do not match.

When the [sex] fields match, the distance of Q and Ri is calculated in the following step. The values of fields peripheral insulin resistance, impaired hepatic glucose up take, excessive hepatic glucose release, insulin secretory defect, age, and weight of Q are represented by vertical vector Vq.

$V_q = (I R q, G U q, G R q, I S q, A q, BM q)^t$ (and t is the transposition matrix)

Where the following obtain.

IRq: Peripheral insulin resistance score
GUq: Impaired hepatic glucose uptake score
GRq: Excessive hepatic glucose release score
ISq: Insulin secretory defect score
Aq: Age
BMq: Weight Similarly, the records Ri obtained from the database represent the vertical vector Vi.

$Vi = (IRi, GUi, GRi, ISi, Ai, BMi)^t$ (and $t$ is the transposition matrix)

The distance d is calculated as the Mahalanobis distance of the vector Vq and vector Vi. The Mahalanobis distance can be considered an indicator having greater similarity compared to Euclidean distance considering the variance of each factor when correlating the factors of the vectors. In order to calculate the Mahalanobis distance, a variance/covariance matrix $\Sigma$ is calculated for all fields of peripheral insulin resistance, impaired hepatic glucose uptake, excessive hepatic glucose release, insulin secretory defect, age, and weight stored in the database ahead of time.

di is determined using $\Sigma$.

$$di = \sqrt{(Vi-Vq)^t \Sigma^{-1}(Vi-Vq)} \quad \text{Equation 1}$$

(and $\Sigma^{-1}$ is the $\Sigma$ inverse matrix.)

The CPU 110a compares the obtained distance d and the minimum value dmin of the distance corresponding to the treatment method M, and proceeds to calculate d as dmin [M] (step S15), and Ri as Rmin [M] (step S16) if the distance d is less than dmin [M].

When dmin[M] obtained for each treatment method is less than a set standard value for each treatment method, the corresponding Rmin [M] is output, and when all dmin [M] are greater than the standard value, there is no corresponding output.

When the Rmin most similar to the relevant pathological condition information is obtained, the treatment effect can be output, for example, in the following manner.

Among the Rmin, the value of the field [treatment effect number] is designated E. This E is used as a query, and all matching records in Table 9 are output. The following SQL language is used in the case of a standard relational database. "SELECT * FROM Table 9 WHERE treatment effect number=E".

The treatment effects and probabilities can be displayed by arranging the obtained codes in ascending order by the value of the [amount of blood sugar decrease] field.

Figure 22:
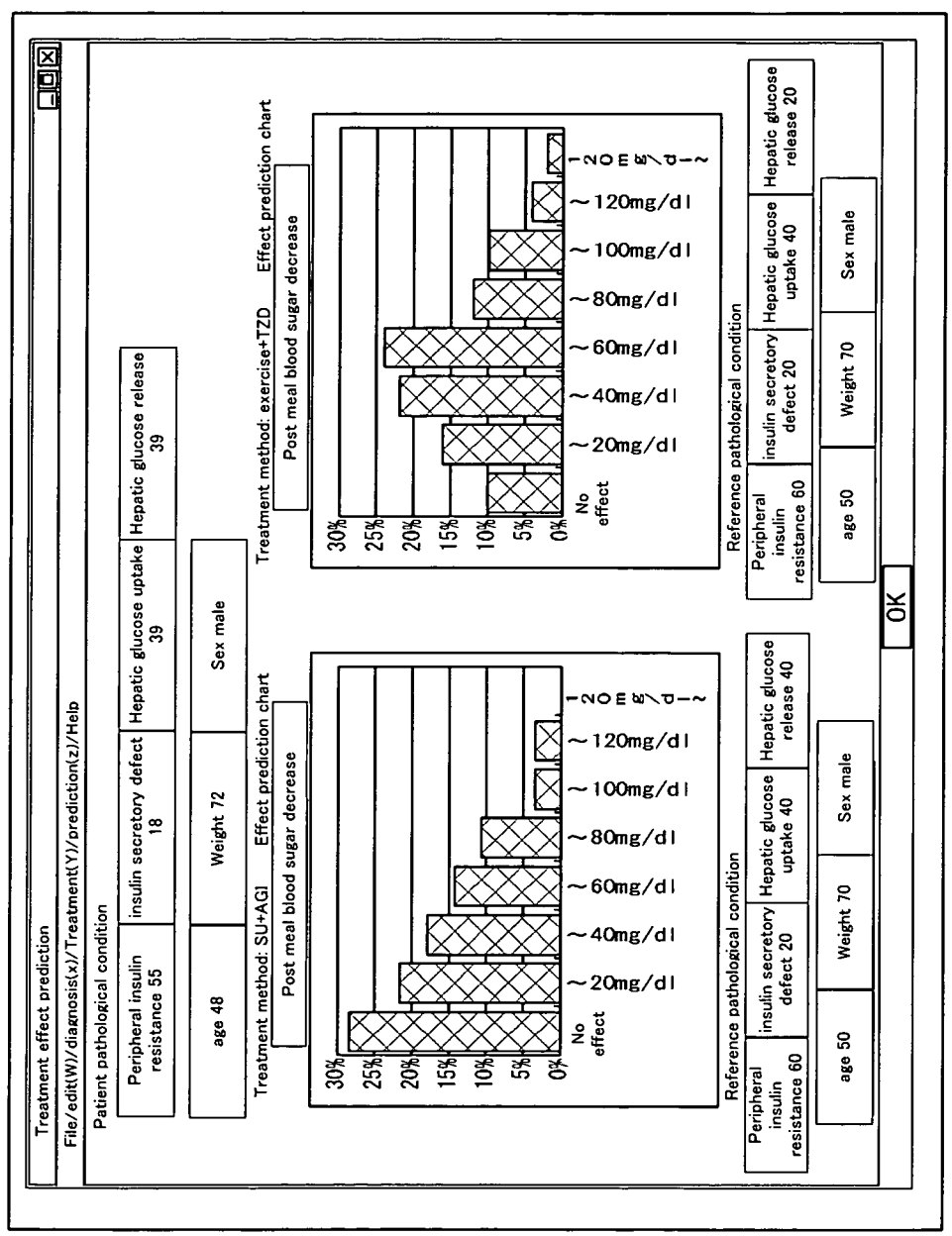
FIG. 22 shows an example of a screen displayed by a display means.

FIG. 22 shows an example of such a display; in this example, the treatment effect predictions are displayed in bar graphs when the Su agent and AGI agent administration is the treatment method, and TZD agent is administered together with an exercise treatment. In each graph, the horizontal axis shows the amount of blood sugar level decrease after meals, and the vertical axis shows the probability of achieving the decrease. The blood sugar level is allocated in increments of 20 mg/dl. The patient pathological condition information is displayed at the upper left of the screen, and representative values (median values of each field used when records are extracted) of the pathological condition information corresponding to the treatment effect are displayed in the lower region. This screen predicts the maximum treatment effect will be obtained by the treatment method combining the administration of TZD agent and an exercise treatment.

Although the time course treatment effect for a predetermined period (for example, six months) after treatment is started is shown in the example shown in FIG. 22, the treatment effect over time can be displayed for treatment effects after one month, three months, six months, and one year if fields for these time periods are provided when creating the database. In this case, the mean values of the treatment effects are calculated for each treatment period (one month, three months and the like), and when the treatment period is plotted on the horizontal axis and the treatment effect is plotted on the vertical axis of the graph, the temporal change of the pathological condition information predicted when using a specific treatment method can be visually comprehended. Furthermore, if the temporal change of the pathological condition information is stored in the database instead of the treatment effect or together with the treatment effect, the temporal change of the pathological condition information predicted using a specific treatment method can be visually comprehended.

What is claimed is:

1. A treatment effect prediction system, comprising:
a processor;
a display device; and
a memory, under control of the processor, including instructions enabling the processor to carry out operations comprising:
simulating a behavior of a living body using a biological model in which an organ function is represented by a numerical model which has a plurality of parameters;

obtaining a parameter which is suitable for a patient from the biological model based on diagnostic data of the patient;

generating a patient pathological condition information, which represents a feature of pathological condition of the patient, based on the parameter;

accessing a database which stores a plurality of pathological condition information, a plurality of treatments and a plurality of treatment effect, wherein each of the plurality of pathological condition information corresponds to at least one of the plurality of treatment effects and each of the plurality of treatment effects corresponds to at least one of the plurality of treatments;

retrieving, from the database, at least one of the plurality of stored pathological condition information that is similar to the patient pathological condition information; and controlling the display device to display the at least one of the plurality of stored treatments and at least one of the plurality of treatment effects which correspond to the retrieved at least one of the plurality of pathological condition information on the display device, wherein the biological model comprises a pancreas block, a liver block, an insulin kinetics block and a peripheral tissue block representing the respective organ function, wherein the liver block receives an input of glucose absorption, an input of blood sugar level from the peripheral tissue block, and an input of insulin secretion rate which is an output from the pancreas block; the insulin kinetics block receives an input of liver-processed insulin from the liver block; the peripheral tissue block receives an input of net glucose release from the liver block, and an input of peripheral tissue insulin concentration from the insulin kinetics block; and the pancreas block receives an input of blood sugar level from the peripheral tissue block, wherein the input and the output of the pancreas block are defined by differential equation $$dY/dt = -\alpha\{Y(t) - \beta(BG(t) - h)\},$$

wherein Y(t) defines a delivery speed of new insulin from a glucose simulation, wherein BG(t) defines a blood sugar level, wherein h defines a glucose concentration threshold of simulated insulin supply, wherein $\alpha$ defines a parameter describing tracking relative to glucose simulation, wherein $\beta$ defines a parameter describing a sensitivity to glucose simulation, and wherein the blood sugar level is higher than the glucose concentration threshold of the simulated insulin supply.

2. The treatment effect prediction system of claim 1, further comprising an input device;

wherein the operations further comprise receiving the diagnostic data via the input device.

3. The treatment effect prediction system of claim 1, wherein the operation of the determining comprises:

simulating a behavior of a living body using a biological model in which an organ function is represented by a numerical model which has a plurality of parameter;

obtaining a parameter which is suitable for the patient from the biological model based on the diagnostic data; and generating the patient pathological condition information based on the parameter.

4. The treatment effect prediction system of claim 1, wherein the database stores a temporal change information of pathological condition occurring when the stored treatment is provided, and the operations further comprise obtaining the temporal change information from the database.

5. The treatment effect prediction system of claim 1, wherein the stored pathological condition information and the stored treatments relate to diabetes.

6. The treatment effect prediction system of claim 5, wherein the stored pathological condition information comprises at least one of information representing insulin secretory defect, information representing peripheral insulin resistance, information representing impaired peripheral glucose uptake, information representing impaired hepatic glucose uptake, and information representing excessive hepatic glucose release.

7. The treatment effect prediction system of claim 1; wherein the operations further comprise:

classifying the treatment effect into a plurality of divisions depending on degree of the effect; and displaying the divisions with frequency or rate of appearance of each division on the display device.

8. The treatment effect prediction system of claim 1, wherein the displaying operation is performed by displaying the stored treatment, the stored treatment effect and the patient pathological condition information on the display device.

9. The treatment effect prediction system of claim 1, wherein the displaying operation is performed by displaying the stored treatment, the stored treatment effect, the retrieved pathological condition and the patient pathological condition information on the display device.

10. A computer program product for the prediction of treatment effects, comprising:

a non-transitory computer readable medium; and computer instructions, on the non-transitory computer readable medium, for enabling a computer to perform the operation of:

simulating a behavior of a living body using a biological model in which an organ function is represented by a numerical model which has a plurality of parameter;

obtaining a parameter which is suitable for a patient from the biological model based on a diagnostic data of the patient;

generating a patient pathological condition information, which represents a feature of pathological condition of the patient, based on the parameter;

accessing a database which stores a plurality of pathological condition information, a plurality of treatments and a plurality of treatment effect, wherein each of the plurality of pathological condition information corresponds to at least one of the plurality of treatment effects and each of the plurality of treatment effects corresponds to at least one of the plurality of treatments;

retrieving, from the database, at least one of the plurality of stored pathological condition information that is similar to the patient pathological condition information; and controlling the computer to display the at least one of the plurality of stored treatments and at least one of the plurality of treatment effects which correspond to the retrieved at least one of the plurality of pathological condition information on a display device of the computer, wherein the biological model comprises a pancreas block, a liver block, an insulin kinetics block and a peripheral tissue block representing the respective organ function, and wherein the liver block receives an input of glucose absorption, an input of blood sugar level from the peripheral tissue block, and an input of insulin secretion rate from the pancreas block; the insulin kinetics block receives an input of liver-processed insulin from the liver block; the peripheral tissue block receives an input of net glucose release from the liver block, and an input of peripheral tissue insulin concentration from the insulin kinetics block; and the pancreas block receives an input of blood sugar level from the peripheral tissue block wherein the input and the output of the pancreas block are defined by differential equation $$dY/dt = -\alpha\{Y(t) - \beta(BG(t) - h)\},$$

wherein Y(t) defines a delivery speed of new insulin from a glucose simulation, wherein BG(t) defines a blood sugar level, wherein h defines a glucose concentration threshold of simulated insulin supply, wherein α defines a parameter describing tracking relative to glucose simulation, wherein β defines a parameter describing a sensitivity to glucose simulation, and wherein the blood sugar level is higher than the glucose concentration threshold of the simulated insulin supply.

11. The computer program product of claim 10, wherein the operation of determining comprises:

simulating a behavior of a living body using a biological model in which an organ function is represented by a numerical model which has a plurality of parameter;

obtaining a parameter which is suitable for the patient from the biological model based on the diagnostic data; and generating the patient pathological condition information based on the parameter.

12. The computer program product of claim 10, wherein the database stores a temporal change information of pathological condition occurring when the stored treatment is provided, and the operations further comprise obtaining the temporal change information from the database.

13. The computer program product of claim 10, wherein the stored pathological condition information and the stored treatments relate to diabetes.

14. The computer program product of claim 10, wherein the operations further comprise:

classifying the treatment effect into a plurality of divisions depending on degree of the effect; and displaying the divisions with frequency or rate of appearance of each division.

15. The computer program product of claim 10, wherein the displaying operation is performed by displaying the stored treatment, the stored treatment effect and the patient pathological condition information on the display device.

16. The computer program product of claim 10, wherein the displaying operation is performed by displaying the stored treatment, the stored treatment effect, the retrieved pathological condition and the patient pathological condition information on the display device.

* * * * *